US012686832B2

(12) United States Patent
M Yasin et al.

(10) Patent No.: US 12,686,832 B2
(45) Date of Patent: Jul. 21, 2026

(54) ASHLESS IONIC LIQUID

(71) Applicant: PETROLIAM NASIONAL BERHAD (PETRONAS), Kuala Lumpur (MY)

(72) Inventors: Farah Fazlina M Yasin, Selangor (MY); Andrea Dolfi, Villastellone (IT); Maria Teresa Sateriale, Villastellone (IT)

(73) Assignee: PETROLIAM NASIONAL BERHAD (PETRONAS), Kuala Lumpur (MY)

(*) Notice: Subject to any disclaimer, the term of this patent is extended or adjusted under 35 U.S.C. 154(b) by 0 days.

(21) Appl. No.: 18/877,084

(22) PCT Filed: Jun. 19, 2023

(86) PCT No.: PCT/MY2023/050048
§ 371 (c)(1),
(2) Date: Dec. 19, 2024

(87) PCT Pub. No.: WO2023/249481
PCT Pub. Date: Dec. 28, 2023

(65) Prior Publication Data
US 2025/0215346 A1 Jul. 3, 2025

(30) Foreign Application Priority Data
Jun. 21, 2022 (MY) ............................ PI2022003306

(51) Int. Cl.
*C10M 133/06* (2006.01)
*C07C 69/48* (2006.01)
(Continued)

(52) U.S. Cl.
CPC ........... *C10M 133/06* (2013.01); *C07C 69/48* (2013.01); *C07C 69/675* (2013.01);
(Continued)

(58) Field of Classification Search
CPC .............. C10M 133/06; C10M 169/04; C10M 2203/003; C10M 2215/26; C10M 141/00;
(Continued)

(56) References Cited

U.S. PATENT DOCUMENTS 4,863,628 A * 9/1989 Nambudiry .......... C11D 10/042 510/130
10,351,760 B2 7/2019 Schultheiss et al.
(Continued)

FOREIGN PATENT DOCUMENTS

CA 2 888 711 A1 7/2014
CA 2 951 371 A1 1/2016
(Continued)

OTHER PUBLICATIONS

International Preliminary Report on Patentability for PCT/MY2023/050048, mailed Dec. 18, 2024.
(Continued)

*Primary Examiner* — Taiwo Oladapo
(74) *Attorney, Agent, or Firm* — Troutman Pepper Locke LLP (Rochester)

(57) ABSTRACT

Provided herein is an ionic liquid comprising: an anionic portion that comprises: at least one carboxylate group; and at least one ester group and/or at least one amide group; and a cationic portion having formula A: A, where: X represents a cationic species; and a and n are selected to approximately balance the charge of the ionic liquid, wherein the ionic liquid is ashless.

16 Claims, 10 Drawing Sheets

(51) Int. Cl.
*C07C 69/675* (2006.01)
*C10M 169/04* (2006.01)
*C10N 20/00* (2006.01)

(52) U.S. Cl.
CPC .... *C10M 169/04* (2013.01); *C10M 2203/003* (2013.01); *C10M 2215/26* (2013.01); *C10N 2020/077* (2020.05)

(58) Field of Classification Search
CPC .. C10M 2203/1025; C10M 2207/2835; C10M 2207/288; C10M 2215/04; C10M 2223/06; C10M 129/76; C07C 69/48; C07C 69/675; C07C 67/08; C07C 69/34; C07C 69/50; C07C 211/63; C10N 2020/077; C10N 2030/06; C10N 2010/02; C10N 2020/071; C07F 9/5407
See application file for complete search history.

(56) References Cited

U.S. PATENT DOCUMENTS

| | | | |
|---|---|---|---|
| 2016/0002569 A1 | 1/2016 | Samsodin et al. | |
| 2017/0218291 A1* | 8/2017 | Reid | C07C 53/10 |
| 2023/0140926 A1 | 5/2023 | Goto | |

FOREIGN PATENT DOCUMENTS

| | | | |
|---|---|---|---|
| EP | 2 961 729 B1 | 6/2019 | |
| EP | 2 819 988 B1 | 12/2020 | |
| JP | 2005309362 A | 11/2005 | |
| RU | 2015 131 112 A | 12/2013 | |
| WO | 2005/056004 A1 | 6/2005 | |
| WO | 2014/009533 A1 | 1/2014 | |
| WO | 2014/133380 A1 | 9/2014 | |
| WO | 2015/140822 A1 | 9/2015 | |
| WO | 2016/010520 A1 | 1/2016 | |
| WO | 2020/172191 A1 | 8/2020 | |
| WO | 2021/005372 A1 | 1/2021 | |
| WO | WO-2021084330 A1 * | 5/2021 | C10M 149/02 |
| WO | 2021/209296 A1 | 10/2021 | |

OTHER PUBLICATIONS

Wu et al., "A Novel One-step Strategy for Extraction and Solidification of Th(IV) Based on Self-assembly Driven by Malonamide-based [DC18DMA]+ Ionic Liquids", Chemical Engineering Journal 430(part 1):132717 (2022).
Tran et al., "Synthesis of Succinimide Based lonic Liquids and Comparison of Extraction Behavior of Co(II) and Ni(II) With Bi-functional lonic Liquids Synthesized by Aliquat336 and Organo-phosphorus Acids", Separation and Purification Technology 238:116496 (2020).
Grecchi et al., "Chiral Biobased Ionic Liquids with Cations or Anions including Bile Acid Building Blocks as Chiral Selectors in Voltammetry," ChemElectroChem 8(7):1377-1387 (2021).
Filipovic et al., "Structural, Biological and Computational Study of Oxamide Derivative," Journal of the Serbian Chemical Society 87(5):545-559 (2022).
Rosca et al., "Spectral and Quantum—Mechanical Characterizations and Biological Activity of N-(P-nitrobenzoyl)-L-phenylalanine," Revis ta de Chimie 67( 6):1062-1067 (2016).
Brotherton-Pleiss et al., "Discovery of Novel Azetidine Amides as Potent Small-Molecule STAT3 Inhibitors," Journal of Medicinal Chemistry 64(1):695-710 (2021).
International Preliminary Report on Patentability for PCT/MY2023/050049, mailed Dec. 18, 2024.
Shevchenko et al., "Protic and Aprotic Anionic Oligomeric Ionic Liquids," Polymer 55:3349-3359 (2014).
Zhou et al., "Ionic Liquids as Lubricant Additives: A Review," ACS Appl. Mater. Interfaces 9:3209-3222 (2017).
International Search Report and Written Opinion for PCT/MY2023/050049, mailed Aug. 28, 2023.
API Standard 1509, Appendix E—API Base Oil Interchangeability Guidelines for Passenger Car Motor Oils and Diesel Engine Oils, REV:01-SEP-2011 pp. E1-E28.
Dong et al., "The Synthesis and Tribological Properties of Dicarboxylic Acid Ionic Liquids," Tribology International 114:132-140 (2017).
Espinosa et al., "Protic Ammonium Carboxylate Ionic Liquid Lubricants of OFHC Copper," Wear 303:495-509 (2013).
Kaisy et al., "Tribological Performance of Low Viscosity Halogen-free Ammonium Based Protic Ionic Liquids with Carboxylate Anions as Neat Lubricants," Tribology International 160:107058 (2021).
Avilés et al., "Diprotic Ammonium Succinate Ionic Liquid in Thin Film Aqueous Lubrication and in Graphene Nanolubricant," Tribology International 67:26 (2019).
Antifriction Additives Market—Global Forecast to 2022, Markets and Markets pp. 1-135 (2018).
Search Report in Maylasia Application No. PI2022003306, dated Aug. 9, 2024.
Substantive Examination Adverse Report in Malaysia Application No. PI2022003306, dated Aug. 9, 2024.
International Search Report and Written Opinion for PCT/MY2023/050048, mailed Oct. 9, 2023.
Extended European Search Report for Europe Application No. 23827585.3, dated Mar. 25, 2026.

* cited by examiner

ASHLESS IONIC LIQUID

This application is a national stage application under 35 U.S.C. § 371 of International Application No. PCT/MY2023/050048, filed 19 Jun. 2023, which claims the priority benefit of Malaysia Application PI2022003306, filed 21 Jun. 2022.

FIELD OF THE INVENTION

The invention relates to an ashless ionic liquid, and to uses and methods involving the ashless ionic liquid.

BACKGROUND

Ionic liquids have been investigated as lubricants and lubricant additives over two decades due to intrinsic properties such as high polarity, low vapor pressure, high thermal stability and tunability. These desirable properties render ionic liquids (ILs) as a possible new generation of friction modifiers, potentially as an alternative to conventional friction modifier/anti-wear additives that typically contain environmentally harmful metal, sulfur and phosphorous species to achieve friction reduction and anti-wear properties. While ILs are effective in reducing friction, they are generally too expensive for large scale use. In addition, many ILs contain halides that cause severe corrosion, rendering them unsuitable for many applications. Other ILs contain metallate-based cations that are toxic and environmentally harmful.

While carboxylic acids have been investigated as starting materials for ionic liquids, they are typically too polar for use in highly non-polar base oils. There is therefore a need for non-toxic and environmentally friendly friction modifiers suitable for use in base oils.

SUMMARY OF THE INVENTION

The inventors have developed a class of ionic liquids derived from carboxylic acids and alcohols/amines that have highly tunable polarity and are suitable for a wide range of uses, such as friction modifiers in base oils. The inventors have also surprisingly found that salts containing the anions used in the ionic liquids may have a range of applications, for example as surfactants.

The invention therefore provides the following numbered clauses.

1. An ionic liquid comprising:

an anionic portion that comprises:

at least one carboxylate group; and at least one ester group and/or at least one amide group; and a cationic portion having formula A:

$$(X)_n^{a+}, \quad A$$

where:

X represents a cationic species; and a and n are selected to approximately balance the charge of the ionic liquid, wherein the ionic liquid is ashless.

2. The ionic liquid according to Clause 1, wherein the anionic portion has:

(a) exactly one carboxylate group and one ester group; or (b) exactly two carboxylate groups and two ester groups; or (c) exactly three carboxylate groups and three ester groups; or (d) exactly four carboxylate groups and four ester groups; or (e) exactly six carboxylate groups and six ester groups.

3. The ionic liquid according to Clause 1, wherein the anionic portion is selected from one or more of formula Ia, formula Ib or formula Ic:

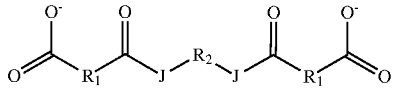

Ia

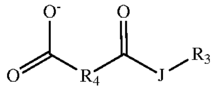

Ib

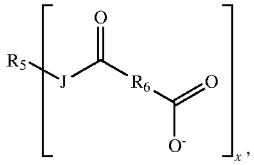

Ic wherein:

x is an integer of from 3 to 6;

each $R_1$ is independently selected from a linear, branched or cyclic $C_1$-$C_{20}$ aliphatic hydrocarbyl group that is saturated or unsaturated, a $C_6$-$C_{10}$ aryl group, and a 5-10 membered heteroaromatic ring system;

$R_2$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ aryl group, a moiety formed by removing two hydroxyl groups from a sugar alcohol, and a moiety formed by removing two hydroxyl groups from a dehydrated sugar alcohol or isosorbide;

$R_3$ is selected from a linear, branched or cyclic $C_1$-$C_{20}$ aliphatic hydrocarbyl group that is saturated or unsaturated;

$R_4$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ (e.g. $C_6$-$C_{10}$) aryl group, and a 5-10 membered heteroaromatic ring system;

$R_5$ is selected from the group consisting of a linear, branched or cyclic $C_1$-$C_{20}$ aliphatic hydrocarbyl group that is saturated or unsaturated, a linear or branched $C_2$-$C_{20}$ polyalkyleneglycol group, a $C_6$-$C_{22}$ aryl group, a moiety formed by removing x hydroxyl groups from a sugar alcohol, and a moiety formed by removing x hydroxyl groups from a dehydrated sugar alcohol; and each $R_5$ independently represents a linear, branched or cyclic $C_1$-$C_{20}$ aliphatic hydrocarbyl group that is saturated or unsaturated, wherein for each of $R_1$ to $R_6$:

each of the $C_1$-$C_{20}$ aliphatic hydrocarbyl group, $C_1$-$C_{40}$ aliphatic hydrocarbyl group, $C_2$-$C_{40}$ polyalkyleneglycol group, and $C_2$-$C_{20}$ polyalkyleneglycol group are not interrupted or are interrupted by one or more groups selected from an aromatic or non-aromatic ring system having from 5 to 14 atoms, an ester group, an amide group, and a carbamate group, and each of the $C_1$-$C_{20}$ aliphatic hydrocarbyl group, $C_1$-$C_{40}$ aliphatic hydrocarbyl group, $C_2$-$C_{40}$ polyalkyleneglycol group, $C_2$-$C_{20}$ polyalkyleneglycol group, and $C_6$-$C_{22}$ aryl group are unsubstituted or substituted by one or more groups selected from the group consisting of hydroxyl, primary amino, secondary amino and tertiary amino, where the secondary and tertiary amino groups are substituted by one or two $C_{1-10}$ hydrocarbyl groups, respectively;

each J independently represents O or $NR_N$, where $R_N$ represents H or a $C_1$-$C_{18}$ alkyl or alkenyl group, optionally wherein one or more of the following applies:

(a) the linear or branched $C_1$-$C_{20}$ aliphatic hydrocarbyl group or $C_1$-$C_{40}$ aliphatic hydrocarbyl group (e.g. $C_1$-$C_{40}$ aliphatic hydrocarbyl group) is substituted by one or more (e.g. one, two or three) hydroxyl groups and one or more (e.g. one, two or three) groups selected from the group consisting of primary amino, secondary amino and tertiary amino;

(b) the $C_2$-$C_{40}$ polyalkyleneglycol is derived from a homopolymer (e.g. is derived from polyethyleneglycol, polypropyleneglycol or polybutyleneglycol);

(c) the $C_2$-$C_{40}$ polyalkyleneglycol is derived from a block copolymer (e.g. is derived from a poly(ethoxylated)(propoxylated)glycol, a poly(propoxylated)(butoxylated)glycol) or a poly(ethoxylated)(butoxylated)glycol; and (d) the linear or branched $C_1$-$C_{20}$ aliphatic hydrocarbyl group or $C_1$-$C_{40}$ aliphatic hydrocarbyl group (e.g. $C_1$-$C_{40}$ aliphatic hydrocarbyl group) is interrupted by one or more (e.g. one, two or three) ester groups and/or is substituted by one or more (e.g. one, two or three) hydroxyl groups.

4. The ionic liquid according to Clause 3, wherein one or more of the following applies:

(a) each $R_1$ is independently selected from a phenyl group, a furan group or, more particularly, a linear or branched $C_4$-$C_{18}$ (e.g. $C_4$-$C_{12}$) aliphatic hydrocarbyl group that is saturated or unsaturated (e.g. a 1,4-valent phenyl group, a 2,5-valent furan group, or more particularly, a linear or branched $C_6$-$C_{10}$ aliphatic hydrocarbyl group that is saturated or unsaturated);

(b) $R_2$ is a moiety formed by removing both hydroxyl groups from isosorbide, or more particularly, a linear or branched $C_2$-$C_{20}$ aliphatic hydrocarbyl group, or a linear or branched $C_2$-$C_{20}$ polyalkyleneglycol, where the linear or branched $C_2$-$C_{20}$ aliphatic hydrocarbyl group and the linear or branched $C_2$-$C_{20}$ polyalkyleneglycol are saturated or unsaturated, where the linear or branched $C_2$-$C_{20}$ aliphatic hydrocarbyl group and the linear or branched $C_2$-$C_{20}$ polyalkyleneglycol are not interrupted or is interrupted by one or more groups selected from an aromatic or non-aromatic ring system having 5 or 6 atoms, an amide group, and a carbamate group;

(c) $R_3$ is selected from a linear or branched $C_1$-$C_{16}$ aliphatic hydrocarbyl group that is saturated or unsaturated;

(d) $R_4$ is selected from a phenyl group, a furan group or, more particularly, a linear or branched $C_4$-$C_{18}$ (e.g. $C_4$-$C_{12}$) aliphatic hydrocarbyl group that is saturated or unsaturated (e.g. a 1,4-valent phenyl group, a 2,5-valent furan group, or more particularly, a linear or branched $C_6$-$C_{10}$ aliphatic hydrocarbyl group that is saturated or unsaturated);

(e) $R_5$ is selected from the group consisting of a linear or branched $C_3$-$C_{14}$ aliphatic hydrocarbyl group that is saturated or unsaturated, a $C_6$-$C_{10}$ aryl group, a moiety formed by removing x hydroxyl groups from a sugar alcohol, and a moiety formed by removing x hydroxyl groups from a dehydrated sugar alcohol; and (f) each $R_6$ is independently selected from a phenyl group, a furan group or, more particularly, a linear or branched $C_4$-$C_{18}$ (e.g. $C_4$-$C_{12}$) aliphatic hydrocarbyl group that is saturated or unsaturated (e.g. a 1,4-valent phenyl group, a 2,5-valent furan group, or more particularly, a linear or branched $C_6$-$C_{10}$ aliphatic hydrocarbyl group that is saturated or unsaturated).

5. The ionic liquid according to Clauses 3 or 4, wherein one or more of the following applies:

(a) each $R_1$ independently represents a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid;

(b) each J represents O and $R_2$ is a group formed by removing two hydroxyl groups from a compound selected from the following:

neopentyl glycol, 1,5-pentanediol, 1,9-nonanediol, 1,6-hexanediol, 2-methyl-1,3-propanediol, 2,5-hexanediol, 2,7-octanediol, a saturated straight chain $C_{28}$ 1,14-diol, an unsaturated straight chain $C_{28}$ 1,14-diol,

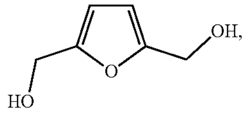

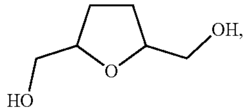

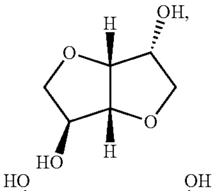

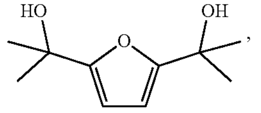

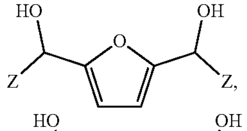
and

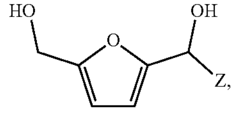

where each Z independently represents a $C_1$ to $C_{12}$ aliphatic hydrocarbyl group;

(c) one of the following applies:

$R_2$ represents a $C_{4-16}$ alkylene group and each J represents NH; or $R_2$ represents propylene, one J represents NH and the other J represents $NR_N$ where $R_N$ represents oleyl;

(d) J is O and $R_3$ is a group formed by removing a hydroxyl group from a compound selected from the group consisting of oleyl alcohol, decanol, Steroyl alcohol, hexadecanol, 1,12-hydroxystearic acid, 1,14-hydroxystearic acid, 1-dodecanol, 2-ethyl-1-hexanol and 2-propylheptanol;

(e) $R_3$ and J together represent a moiety formed by removing an amino hydrogen atom from a compound selected from the group consisting of oleylamine, dodecylamine, tetradecylamine, decylamine, dioctylamine, didecylamine, dihexylamine, 2-ethyl-1-hexylamine and diisobutylamine;

(f) each $R_4$ represents a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid;

(g) $R_5$ is selected from the group consisting of a phenyl ring, and a branched $C_3$-$C_{10}$ aliphatic group; and (h) each $R_6$ independently represents a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid; and (i) x is 3, 4 or 6 (e.g. x is 3).

6. The ionic liquid according to any one of Clauses 3 to 5, wherein one of the following applies:

(a) x is 3 and $R_5$ is a moiety formed by removing three hydroxyl groups from a compound selected from the group consisting of trimethylolpropane, glycerol, pyrogallol, hydroxyquinol, phloroglucinol, and 3-methylpentane-1,3,5-triol;

(b) x is 4, and $R_5$ is a moiety formed by removing four hydroxyl groups from a compound selected from the group consisting of sorbitan, pentaerythritol, di(trimethylolpropane) and di(glycerol); and (c) x is 6, and $R_5$ is a moiety formed by removing six hydroxyl groups from a compound selected from the group consisting of sorbitol, di-pentaerythritol, mannitol, and glucose.

7. The ionic liquid according to any one of Clauses 3 to 6, wherein at least one of the following applies:

each $R_1$ independently represents a linear or branched $C_4$-$C_{12}$ (e.g. $C_6$-$C_{10}$) alkylene group;

$R_2$ represents a linear or branched $C_2$-$C_{12}$ (e.g. $C_3$-$C_{10}$) alkylene group;

$R_3$ represents a linear or branched $C_4$-$C_{12}$ (e.g. $C_6$-$C_{10}$) alkyl group;

$R_4$ represents a linear or branched $C_4$-$C_{12}$ (e.g. $C_6$-$C_{10}$) alkylene group;

$R_5$ represents a saturated linear or branched $C_2$-$C_8$ (e.g. $C_3$-$C_6$) hydrocarbon linking group; and each $R_6$ independently represents a linear or branched $C_2$-$C_{10}$ (e.g. $C_6$-$C_{10}$) alkylene group.

8. The ionic liquid according to any one of Clauses 3 to 7, wherein at least one of the following applies:

$R_1$ represents a linear alkylene group; and $R_1$ represents a $C_8$ or $C_{10}$ alkylene group (e.g. a linear $C_8$ or $C_{10}$ alkylene group).

9. The ionic liquid according to any one of Clauses 3 to 7, wherein $R_2$ represents a branched alkylene group, optionally wherein $R_2$ represents a moiety having the formula:

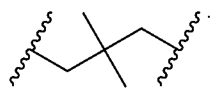 [SMILES: *CC(C)(C)C*]

10. The ionic liquid according to any one of Clauses 3 to 7, wherein:

$R_3$ represents a linear alkyl group, and/or $R_3$ represents a $C_8$ or $C_{10}$ alkyl group, (e.g. a linear $C_{10}$ alkyl group).

11. The ionic liquid according to any one of Clauses 3 to 7, wherein:

$R_4$ represents a linear alkylene group, and/or $R_4$ represents a $C_6$-$C_8$ alkylene group (e.g. a linear $C_7$ alkylene group).

12. The ionic liquid according to any one of Clauses 3 to 7, wherein $R_5$ represents a branched group, optionally wherein $R_5$ represents a moiety having the formula:

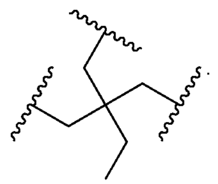

13. The ionic liquid according to any one of Clauses 3 to 7, wherein:

$R_5$ represents a linear alkylene group, and/or $R_6$ represents a $C_8$ or $C_{10}$ alkyl group (e.g. a linear $C_8$ alkylene group).

14. The ionic liquid according to any one of Clauses 3 to 9, wherein the anionic portion is of formula Ia.

15. The ionic liquid according to any one of any one of Clauses 3 to 7, 10 and 11, wherein the anionic portion is of formula Ib.

16. The ionic liquid according to any one of any one of Clauses 3 to 7, 12 and 13, wherein the anionic portion is of formula Ic and x is 3, optionally wherein the anionic portion is of formula Ici:

Ici

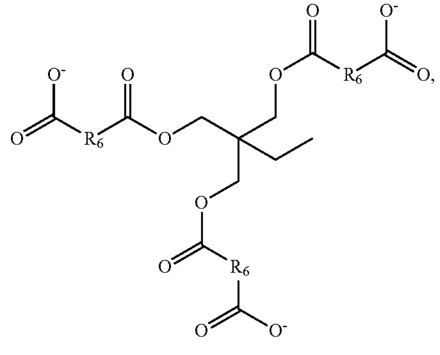

where $R_5$ is as defined in any one of Clauses 3 to 7.

17. The ionic liquid according to any one of the preceding clauses, wherein the cationic portion is selected from one or more of the group consisting of a quaternary phosphonium cation, a quaternary sulphonium cation, a quaternary ammonium cation comprising at least one amide group, a quaternary ammonium cation comprising at least one ester group, a substituted quaternary imidazolium cation comprising at least one ester group, a substituted quaternary imidazolium cation comprising at least one alkyleneglycol group, a substituted quaternary imidazolium cation comprising at least one amide group, azaannulenium, azathiazolium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dibenzofuranium, dibenzothiophenium, dithiazolium, dithiazolium, furanium, guanidinium, imidazolium, indazolium, indolinium, indolium, morpholinium, oxaborolium, oxaphospholium, oxazinium, oxazolium, iso-oxazolium, oxazolinium, pentazolium oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, isoquinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, combinations thereof, and cationic molecules comprising more than one of the foregoing.

18. The ionic liquid according to any one of the preceding clauses, wherein the cationic portion has the formula $[YX_3X_4X_5X_6]^+$, wherein:

Y represents N, P or S (e.g. N or P); and (a) each of $X_3$ to $X_6$ are independently selected from $C_1$ to $C_{30}$ straight chain or branched alkyl and alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$ to $X_6$ combine to form an alkylene chain $—(CH_2)_q—$ wherein q is from 3 to 6; wherein any one or more of said straight or branched chain alkyl and alkenyl groups, cycloalkyl groups, arylalkyl groups, alkylaryl groups; aryl groups or alkylene chains are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl; or (b) at least one of $X_3$ to $X_6$ have the formula $—X_7(C{=}O)X_8$ or $—X_7(C{=}O)—O—X_8$, wherein $X_7$ is a $C_1$ to $C_{10}$ straight chain or branched alkyl or alkenyl group, or a $C_3$ to $C_6$ cycloalkyl or cycloalkenyl group; and $X_8$ is a $C_1$ to $C_{30}$ straight chain or branched alkyl or alkenyl group; a $C_3$ to $C_6$ cycloalkyl group; a $C_1$ to $C_{30}$ arylalkyl group; a $C_1$ to $C_{30}$ alkylaryl group; an aryl group; or any two respective $X_8$ groups combine to form an alkylene chain $—(CH_2)_q—$ wherein q is from 3 to 6; wherein $X_7$ and/or $X_8$ are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl;

and wherein the other of $X_3$ to $X_6$ that are not as defined above are independently selected from $C_1$ to $C_{30}$ straight chain or branched alkyl and alkenyl groups such as $C_1$ to $C_{10}$ alkyl or alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$, $X_4$, $X_5$ and $X_6$ combine to form an alkylene chain $—(CH_2)_q—$ wherein q is from 3 to 6; wherein any one or more of said straight or branched chain alkyl and alkenyl groups, cycloalkyl groups, arylalkyl groups, alkylaryl groups; aryl groups or alkylene chains is optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl.

19. The ionic liquid according to Clause 18, wherein option (a) applies.

20. The ionic liquid according to Clause 18 or 19, wherein each of $X_3$ to $X_6$ independently represent $C_1$ to $C_{30}$ straight chain or branched alkyl and alkenyl groups, optionally $C_1$ to $C_{30}$ straight chain or branched alkyl groups, more optionally $C_4$ to $C_{18}$ straight chain or branched alkyl groups, such as $C_4$ to $C_{18}$ straight chain alkyl groups.

21. The ionic liquid according to any one of Clauses 18 to 20, wherein:

$X_3$ to $X_5$ are the same and $X_6$ is different to $X_3$ to $X_5$, optionally wherein $X_6$ represents methyl, and each of $X_3$ to $X_5$ represent octyl.

22. The ionic liquid according to any one of Clauses 18 to 20, wherein each of $X_3$ to $X_6$ are the same, optionally wherein each of $X_3$ to $X_6$ represents butyl.

23. The ionic liquid according to any one of Clauses 18 to 22, wherein Y represents N.

24. The ionic liquid according to any one of Clauses 1 to 22, wherein the cationic portion is selected from the group consisting of:

trioctyl methyl ammonium; tetrabutylphosphonium; trioctylmethyl phosphonium; tetraoctyl ammonium; dioctadecyldiammonium; and

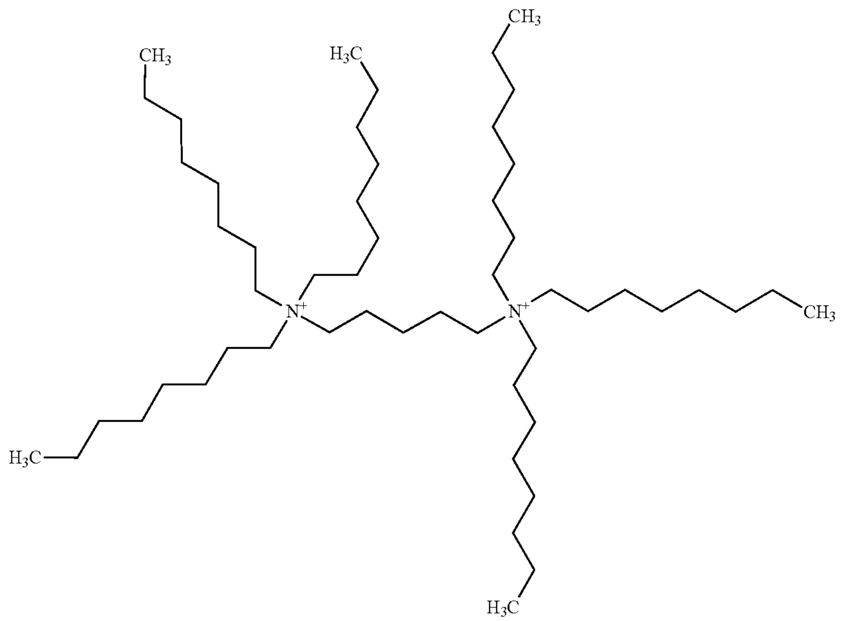 [SMILES: CCCCCCCC[N+](CCCCCCCC)(CCCCCCCC)CCCCC[N+](CCCCCCCC)(CCCCCCCC)CCCCCCCC]

optionally wherein the cationic portion is tetrabutylphosphonium.

25. A composition comprising:
a base fluid (e.g. a base oil comprising a base stock selected from the group consisting of a Group I base stock, a Group II base stock, a Group III base stock, a Group IV base stock, a Group V base stock, and combinations thereof; a base fuel; or a solvent), and
an ionic liquid as defined in any one of Clauses 1 to 24.

26. The composition according to Clause 25, wherein the composition comprises from 0.01 to 10 wt. % (e.g. 0.1 to 5 wt. %) ionic liquid.

27. Use of an ionic liquid as defined in any one of Clauses 1 to 24 as a friction modifier additive in a base fluid (e.g. a base oil comprising a base stock selected from the group consisting of a Group I base stock, a Group II base stock, a Group III base stock, a Group IV base stock, a Group V base stock, and combinations thereof; a base fuel; or a solvent) or in a polyol ester.

28. A method of reducing the friction of a base fluid (e.g. a base oil comprising a base stock selected from the group consisting of a Group I base stock, a Group II base stock, a Group III base stock, a Group IV base stock, a Group V base stock, and combinations thereof; a base fuel; or a solvent) or of a polyol ester (e.g. a method of reducing the friction of a polyol ester), said method comprising the steps:
(i) providing a base oil or a polyol ester;
(ii) mixing the base oil or polyol ester with an appropriate amount of an ionic liquid as defined in any one of Clauses 1 to 24.

29. A method of preparing an ionic liquid as defined in any one of Clauses 1 to 24, said method comprising the steps:
(i) providing an intermediate product comprising:
an ester group or an amide group (e.g. an ester group); and
a carboxylic acid group
(e.g. by reacting an alcohol or amine (e.g. an alcohol) with a dicarboxylic acid to produce said intermediate product);
(ii) converting the intermediate product to an ionic liquid by either:
(a) directly reacting the intermediate product with a cationic base (e.g. a tetraalkyl ammonium hydroxide, a tetraalkyl phosphonium hydroxide, a tetraalkyl ammonium methylcarbonate, or a tetraalkyl phosphonium methylcarbonate);
(b) deprotonating the intermediate esters with a base (e.g. LiOH, NaOH, $NaHCO_3$ or KOH) to form an ester alkaline/metal salts, subsequently conducting a metathesis reaction between the ester salt with a salt compound that comprises a cationic portion having formula A; or
(c) reacting the intermediate product with an alkylamine or arylamine, optionally wherein the alkylamine is selected from the group consisting of:
$C_1$-$C_{20}$ alkyl-mono alkyl amines that are saturated or unsaturated (e.g. oleyl amine, decylamine, tetradecyl amines);
$C_1$-$C_{20}$ alkyl-dialkyl amines that are saturated or unsaturated, (e.g. diisopropylamine, dioctyl amine, dioleylamine, diphenyl amine); and
$C_1$-$C_{20}$ alkyl-trialkyl amines that are saturated or unsaturated, (e.g. N,N-dimethyl octyl amine, N,N-dimethyl phenyl amine).

30. The method according to Clause 29, wherein the alcohol is selected from the group consisting of a monoalcohol, a diol and a triol.

31. The method according to Clause 29 or 30, wherein the method comprises:
reacting an alcohol with a dicarboxylic acid to produce the intermediate product; and
a preliminary step of choosing the alcohol and dicarboxylic acid based on a desired polarity of the ionic liquid.

32. The method according to any one of Clauses 29 to 31, wherein the alcohol and dicarboxylic acid are chosen to provide an ionic liquid having a desired solubility in a base oil or polyol ester.

33. A salt comprising:

an anionic portion as defined in any one of Clauses 1 to 16, and a cationic portion comprising one or more alkali metal cations (e.g. Li, $Na^+$ or $K^+$).

34. A method of preparing a salt as defined in Clause 33, said method comprising the steps:

(i) reacting an alcohol with a dicarboxylic acid to produce an intermediate product comprising an ester group and a carboxylic acid group;

(ii) reacting the intermediate product with a basic salt of an alkali metal (e.g. a basic lithium, sodium or potassium salt, such as LiOH, NaOH, $NaHCO_3$ or KOH) to form a salt as defined in Clause 33.

DETAILED DESCRIPTION OF THE INVENTION

Figure 1:
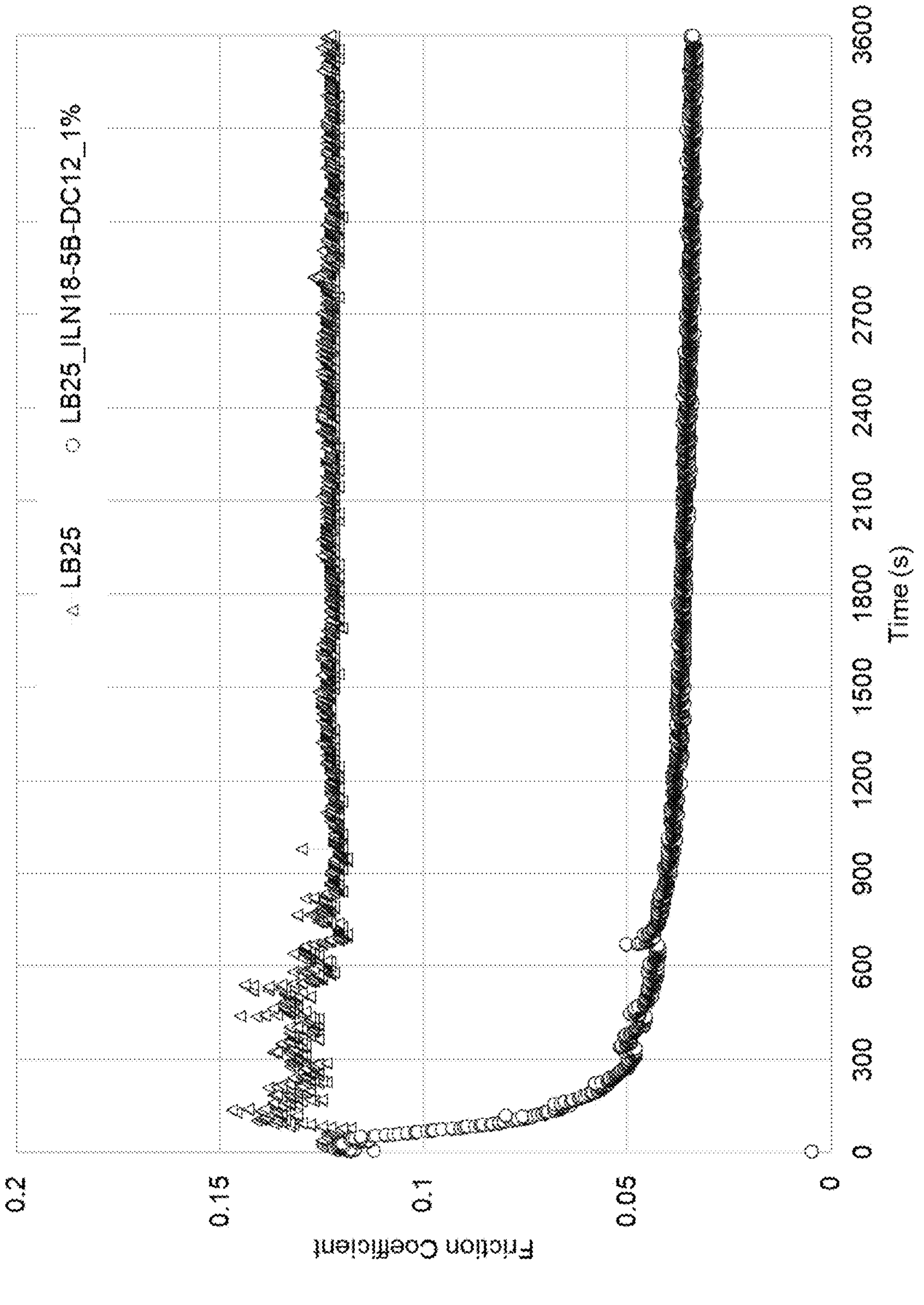
FIG. 1 shows friction coefficient behaviour for an ionic liquid according to the invention (ILN18-5B-DC12) in a polar polyol ester base oil (Petronas LB 25).

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The phrase "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure.

The invention provides an ionic liquid comprising:

an anionic portion that comprises:

at least one carboxylate group; and at least one ester group and/or at least one amide group; and a cationic portion having formula A:

$$(X)_n^{a+}, \qquad \text{A}$$

where:

X represents a cationic species; and a and n are selected to approximately balance the charge of the ionic liquid, wherein the ionic liquid is ashless.

As used herein, the term "ionic liquid" refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., preferably below 150° C., particularly below 100° C., around room temperature (15 to 30° C.), or even below 0° C. Ionic liquids having melting points below around 30° C. are commonly referred to as "room temperature ionic liquids". In room temperature ionic liquids, the structures of the cation and anion prevent the formation of an ordered crystalline structure and therefore the salt is liquid at room temperature. In some embodiments of the invention, the ionic liquid is liquid at a temperature of below 100° C.

Ionic liquids are most widely known as solvents, because of their negligible vapour pressure, temperature stability, low flammability and recyclability make them environmentally friendly. Due to the vast number of anion/cation combinations that are available it is possible to fine-tune the physical properties of the ionic liquid (e.g. melting point, density, viscosity, and miscibility with water or organic solvents) to suit the requirements of a particular application.

The ionic liquids of the present invention utilises a dual carboxylate and ester/amide functionality. This advantageously provides an anionic portion that has multiple organic chains, the length of which may be adjusted to fine tune the polarity of the ionic liquid for the desired application, as discussed above. The use of ester/amide linkages also enables the ionic liquids to be advantageously biodegradable and environmentally friendly, as well as being easy to synthesise using green processes.

As used herein, an "ashless" ionic liquid is an ionic liquid that does not leave an ash/inflammable residue upon combustion. In some embodiments of the invention, an ashless ionic liquid may leave less than 1 wt. % uncombusted residue, such as less than 0.7 wt. %, less than 0.5 wt. % or less than 0.1 wt. %. In some embodiments of the invention that may be mentioned herein, an ashless ionic liquid may be free of (e.g. comprise less than 1 wt. %, less than 0.1 wt. %, less than 0.01 wt. %, less than 0.001 wt. % or less than 0.0001 wt. %) sulfur-containing compounds, metals, or metal ion-containing compounds.

The ionic liquid comprises an anionic portion that comprises:

at least one carboxylate group; and at least one ester group and/or at least one amide group.

In some embodiments of the invention that may be mentioned herein, the anionic portion have:

(a) exactly one carboxylate group and one ester group; or (b) exactly two carboxylate groups and two ester groups; or (c) exactly three carboxylate groups and three ester groups; or (d) exactly four carboxylate groups and four ester groups; or (e) exactly six carboxylate groups and six ester groups.

In some embodiments of the invention that may be mentioned herein, the anionic portion may be selected from one or more of formula Ia, formula Ib or formula Ic:

Ia

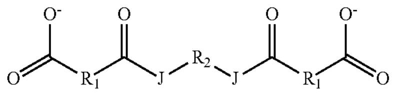

Ib

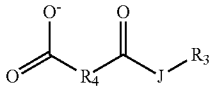

Ic

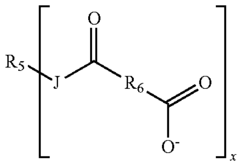

wherein:

x is an integer of from 3 to 6;

each $R_1$ is independently selected from a linear, branched or cyclic $C_1$-$C_{20}$ aliphatic hydrocarbyl group that is saturated or unsaturated, a $C_6$-$C_{10}$ aryl group, and a 5-10 membered heteroaromatic ring system;

$R_2$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ aryl group, a moiety formed by removing two hydroxyl groups from a sugar alcohol, and a moiety formed by removing two hydroxyl groups from a dehydrated sugar alcohol or isosorbide;

$R_3$ is selected from a linear, branched or cyclic $C_1$-$C_{20}$ aliphatic hydrocarbyl group that is saturated or unsaturated;

$R_4$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ (e.g. $C_6$-$C_{10}$) aryl group, and a 5-10 membered heteroaromatic ring system;

$R_5$ is selected from the group consisting of a linear, branched or cyclic $C_1$-$C_{20}$ aliphatic hydrocarbyl group that is saturated or unsaturated, a linear or branched $C_2$-$C_{20}$ polyalkyleneglycol group, a $C_6$-$C_{22}$ aryl group, a moiety formed by removing x hydroxyl groups from a sugar alcohol, and a moiety formed by removing x hydroxyl groups from a dehydrated sugar alcohol; and each $R_6$ independently represents a linear, branched or cyclic $C_1$-$C_{20}$ aliphatic hydrocarbyl group that is saturated or unsaturated, wherein for each of $R_1$ to $R_6$:

each of the $C_1$-$C_{20}$ aliphatic hydrocarbyl group, $C_1$-$C_{40}$ aliphatic hydrocarbyl group, $C_2$-$C_{40}$ polyalkyleneglycol group, and $C_2$-$C_{20}$ polyalkyleneglycol group are not interrupted or are interrupted by one or more groups selected from an aromatic or non-aromatic ring system having from 5 to 14 atoms, an ester group, an amide group, and a carbamate group, and each of the $C_1$-$C_{20}$ aliphatic hydrocarbyl group, $C_1$-$C_{40}$ aliphatic hydrocarbyl group, $C_2$-$C_{40}$ polyalkyleneglycol group, $C_2$-$C_{20}$ polyalkyleneglycol group, and $C_6$-$C_{22}$ aryl group are unsubstituted or substituted by one or more groups selected from the group consisting of hydroxyl, primary amino, secondary amino and tertiary amino, where the secondary and tertiary amino groups are substituted by one or two $C_{1-10}$ hydrocarbyl groups, respectively;

each J independently represents O or $NR_N$, where $R_N$ represents H or a $C_1$-$C_1$C alkyl or alkenyl group.

As used herein, the term "hydrocarbyl" refers to a radical hydrocarbon group, which radical has the valency that will be obvious to a person skilled in the art from the general formula in which the radical is present. In some embodiments of the invention that may be mentioned herein, a hydrocarbyl group may be an aliphatic hydrocarbyl group, such as alkyl/alkylene, alkenyl/alkenylene, and alkynyl/alkynylene, and equivalent groups having a valency of three or more. In a particular embodiment of the invention that may be mentioned herein, a hydrocarbyl group may be a saturated aliphatic group, e.g. an alkyl/alkylene group.

Moieties defined and referred to herein have a valency that will be obvious to a person skilled in the art from the context used. For example, a radical present in a general formula having a single covalent bond from the radical to another moiety will have a valency of one, while a radical present in a general formula having two covalent bonds from the radical to other moieties will have a valency of two. This can be defined generally as a radical present in a general formula having x covalent bonds from the radical to other moieties in the general formula will have a valency of x. By way of example, if the term "alkyl" is used herein in a context that requires two covalent bonds to be formed from the "alkyl" moiety, then the term alkyl in said context is intended to refer to a bivalent radical.

As used herein, an "aliphatic" group is a group that does not comprise an aromatic ring.

An "aromatic" ring refers to a planar ring system comprising 4n+2 delocalised electrons in the pi system, where n is an integer.

Unless otherwise stated, the term "aryl" when used herein includes $C_6$-$C_{14}$ (such as $C_6$-$C_{10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

As used herein, a "heteroaromatic" group or ring system refers to an aromatic group comprising at least one endocyclic atom that is not carbon. For example, an aromatic group comprising at least one endocyclic atom selected from the group consisting of N, O, and S.

As used herein, "interrupted" in the context of a group defined herein means that one or more covalent bonds in said group is replaced by a moiety as defined. When a group having a defined number of carbon atoms is interrupted by a carbon-containing group, the carbon atoms of said interrupting group do not count towards the number of carbon atoms of said interrupted group. For the avoidance of doubt, an aliphatic group as defined herein may be interrupted by an aromatic group.

Moieties defined herein may be interrupted by one or more groups (e.g. from 1 to 5 groups, from 1 to 4 groups, from 1 to 3 groups, from 1 to 2 groups, or 1 group). For example, moieties defined herein may be interrupted by one or more groups selected from an aromatic or non-aromatic ring system having from 5 to 14 atoms, an ester group, an amide group, and a carbamate group. In some embodiments, the interrupting group may be an aromatic or non-aromatic ring system having from 5 to 14 atoms. In some embodiments, he interrupting group may be an ester group, an amide group, or a carbamate group.

Suitable interrupting aromatic or non-aromatic ring systems having from 5 to 14 atoms include cycloalkyl groups, cycloalkenyl groups, heterocycloalkyl groups, heterocycloalkenyl groups, aryl groups, and heteroaromatic groups having from 5 to 14 atoms in the ring system, such as from 5 to 10 atoms. In a specific embodiment of the invention that may be mentioned herein, the interrupting aromatic or non-aromatic ring system having from 5 to 14 atoms may be selected from aromatic and heteroaromatic groups having 5 or 6 atoms in the ring system, such as aryl and furan. Interrupting aromatic or non-aromatic ring systems may themselves be substituted as defined herein. In such cases, the number of atoms of the substituent does not count towards the number of atoms in the aromatic or non-aromatic ring system, which is from 5 to 14 atoms.

Moieties defined herein may also be interrupted by an ester group, said an amide group, or a carbamate group.

In this context, an ester group means —O—C(═O)— or —C(═O)—O—.

In this context, an amide group means —$NR_{Na}$—C(═O)— or —C(═O)—$NR_{Na}$—, where $R_{Na}$ is a $C_{1-6}$ alkyl group.

In this context, a carbamate group means —$NR_{Na}$—C(═O)—O— or —O—C(═O)—$NR_{Na}$—, where $R_{Na}$ is a $C_{1-6}$ alkyl group.

As used herein, "substituted" in the context of a group defined herein means that one or more hydrogen atoms in said group is replaced by a substituting moiety. When a group having a defined number of carbon atoms is substituted by a carbon-containing group, the carbon atoms of said substituting group do not count towards the number of carbon atoms of said substituted group. Moieties defined herein may be substituted by any appropriate number of groups as defined herein, for example from 1 to 5 groups, from 1 to 4 groups, from 1 to 3 groups, from 1 to 2 groups, or 1 group. Examples of suitable substituents include hydroxy, amino (whether primary, secondary or tertiary), hydrocarbyl groups (e.g. $C_{1-20}$, such as $C_{1-10}$ hydrocarbyl)

As used herein "polyalkyleneglycol" refers to a moiety of the formula —[O—R]$_n$—O, or where the context requires, H—[O—R]$_n$—O—H, where R represents an alkylene group (e.g. a $C_{1-10}$ or $C_{14}$ alkylene) and n represents an integer. A polyalkyleneglycol may comprise different R groups, or may comprise R groups that are all identical. A skilled person would easily understand from context when "polyalkyleneglycol" is intended to refer to a moiety —[O—R]$_n$—O—, e.g. when a bivalent moiety represents a polyalkyleneglycol group.

In some embodiments that may be mentioned herein, a polyalkyleneglycol chain in the ionic liquid may be derived from a homopolymer (e.g. is derived from polyethyleneglycol, polypropyleneglycol or polybutyleneglycol).

In some embodiments that may be mentioned herein, a polyalkyleneglycol chain in the ionic liquid may be derived from a block copolymer (e.g. is derived from a poly(ethoxylated)(propoxylated)glycol, a poly(propoxylated)(butoxylated)glycol) or a poly(ethoxylated)(butoxylated)glycol).

As used herein, "alkyl" refers to an unbranched or branched, cyclic, saturated hydrocarbyl radical, which may be substituted or unsubstituted.

As used herein, "alkenyl" refers to an unbranched or branched, cyclic, unsaturated hydrocarbyl radical, which may be substituted or unsubstituted. As used herein, an alkenyl group may comprise one, or more than one, carbon-carbon double bonds or carbon-carbon triple bonds. For the avoidance of doubt, the term "alkenyl" as used herein is intended to cover groups comprising C—C triple bonds (also known as alkynyl groups).

In the embodiments of the invention discussed below, for each of $R_1$ to $R_6$:

- each of the $C_1$-$C_{20}$ aliphatic hydrocarbyl group, $C_1$-$C_{40}$ aliphatic hydrocarbyl group, $C_2$-$C_{40}$ polyalkyleneglycol group, and $C_2$-$C_{20}$ polyalkyleneglycol group may be not interrupted or may be interrupted by one or more groups selected from an aromatic or non-aromatic ring system having from 5 to 14 atoms, an ester group, an amide group, and a carbamate group, and
- each of the $C_1$-$C_{20}$ aliphatic hydrocarbyl group, $C_1$-$C_{40}$ aliphatic hydrocarbyl group, $C_2$-$C_{40}$ polyalkyleneglycol group, $C_2$-$C_{20}$ polyalkyleneglycol group, and $C_6$-$C_{22}$ aryl group may be unsubstituted or substituted by one or more groups selected from the group consisting of hydroxyl, primary amino, secondary amino and tertiary amino, where the secondary and tertiary amino groups are substituted by one or two $C_{1-10}$ hydrocarbyl groups, respectively.

In some embodiments of the invention, the anionic portion is an anionic species of formula Ia:

Ia

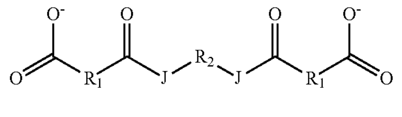

In general, each $R_1$ is independently selected from a linear or branched $C_1$-$C_{20}$ aliphatic hydrocarbyl group that is saturated or unsaturated, a $C_6$-$C_{10}$ aryl group, and a 5-10 membered heteroaromatic ring system.

In some embodiments of the invention that may be mentioned herein, each $R_1$ may be independently selected from a phenyl group, a furan group or, more particularly, a linear or branched $C_4$-$C_{18}$ (e.g. $C_4$-$C_{12}$) aliphatic hydrocarbyl group that is saturated or unsaturated. For example, a 1,4-valent phenyl group, a 2,5-valent furan group, or more particularly, a linear or branched $C_6$-$C_{10}$ aliphatic hydrocarbyl group that is saturated or unsaturated (e.g. a linear or branched $C_6$-$C_{10}$ alkylene group that is saturated or unsaturated).

In some embodiments of the invention that may be mentioned herein, each $R_1$ may independently represent a linear or branched $C_4$-$C_{18}$ (e.g. $C_4$-$C_{12}$) alkylene group.

In some embodiments of the invention that may be mentioned herein, each $R_1$ may independently represent a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid.

In some embodiments of the invention that may be mentioned herein, each $R_1$ may independently represent a linear or branched $C_4$-$C_{12}$ (e.g. $C_6$-$C_{10}$) alkylene group.

In some embodiments of the invention that may be mentioned herein $R_1$ may represent a linear alkylene group.

In some embodiments of the invention that may be mentioned herein $R_1$ may represent a $C_8$ or $C_{10}$ alkylene group (e.g. a linear $C_8$ or $C_{10}$ alkylene group).

In general, $R_2$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ aryl group, a moiety formed by removing two hydroxyl groups from a sugar alcohol, and a moiety formed by removing two hydroxyl groups from a dehydrated sugar alcohol or isosorbide.

In some embodiments of the invention that may be mentioned herein, $R_2$ may be selected from the group consisting of a moiety formed by removing both hydroxyl groups from isosorbide, or more particularly, a linear or branched $C_2$-$C_{20}$ aliphatic hydrocarbyl group and a linear or branched $C_2$-$C_{20}$ polyalkyleneglycol, where the linear or branched $C_2$-$C_{20}$ aliphatic hydrocarbyl group and the linear or branched $C_2$-$C_{20}$ polyalkyleneglycol are saturated or unsaturated, where the linear or branched $C_2$-$C_{20}$ aliphatic hydrocarbyl group and the linear or branched $C_2$-$C_{20}$ polyalkyleneglycol are not interrupted or is interrupted by one or more groups selected from an aromatic or non-aromatic ring system having 5 or 6 atoms, an amide group, and a carbamate group.

In some embodiments of the invention that may be mentioned herein, $R_2$ may represent a moiety formed by removing both hydroxyl groups from isosorbide, or more particularly, a linear or branched $C_3$-$C_{16}$ aliphatic hydrocarbyl group that is saturated or unsaturated, which hydrocarbyl group is not interrupted or is interrupted by one or more groups selected from an aromatic or non-aromatic ring system having 5 or 6 atoms. For example, $R_2$ may represent a moiety formed by removing both hydroxyl groups from isosorbide, or more particularly, a linear or branched $C_{3-10}$ aliphatic hydrocarbyl group.

In some embodiments of the invention that may be mentioned herein, each J may represent O and $R_2$ may represent a moiety formed by removing both hydroxyl groups from a compound selected from the following:

neopentyl glycol, 1,5-pentanediol, 1,9-nonanediol, 1,6-hexanediol, 2-methyl-1,3-propanediol, 2,5-hexanediol, 2,7-octanediol, a saturated straight chain $C_{28}$ 1,14-diol, an unsaturated straight chain $C_{28}$ 1,14-diol,

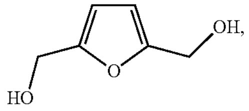 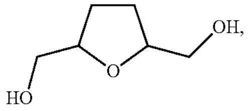

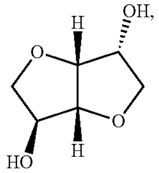 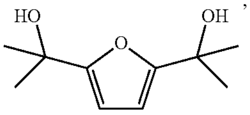

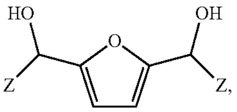 and 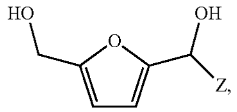

where each Z independently represents a $C_1$ to $C_{12}$ aliphatic hydrocarbyl group.

In some embodiments of the invention that may be mentioned herein, $R_2$ may represent a $C_{4-16}$ alkylene group and each J represents NH.

In some embodiments of the invention that may be mentioned herein, $R_2$ may represent propylene, one J may represent NH and the other J may represent $NR_N$ where $R_N$ represents oleyl.

In some embodiments of the invention that may be mentioned herein, $R_2$ may represent a linear or branched $C_2$-$C_{12}$ (e.g. $C_3$-$C_{10}$) alkylene group.

In some embodiments of the invention that may be mentioned herein, $R_2$ may represent a branched alkylene group.

In some embodiments of the invention that may be mentioned herein, $R_2$ may represent a moiety having the formula:

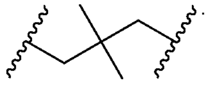 [SMILES: *CC(C)(C)C*]

In some embodiments of the invention, the anionic portion is an anionic species of formula Ib:

Ib

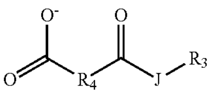

In general, $R_3$ is selected from a linear, branched or cyclic $C_1$-$C_{20}$ aliphatic hydrocarbyl group that is saturated or unsaturated.

In some embodiments of the invention that may be mentioned herein, $R_3$ may be selected from a linear or branched $C_1$-$C_{16}$ aliphatic hydrocarbyl group that is saturated or unsaturated.

In some embodiments of the invention that may be mentioned herein, J may be O and $R_3$ may be a group formed by removing a hydroxyl group from a compound selected from the group consisting of oleyl alcohol, decanol, stearoyl alcohol, hexadecanol, 1,12-hydroxystearic acid, 1,14-hydroxystearic acid, 1-dodecanol, 2-ethyl-1-hexanol and 2-propylheptanol.

In some embodiments of the invention that may be mentioned herein, $R_3$ and J may together represent a moiety formed by removing an amino hydrogen atom from a compound selected from the group consisting of oleylamine, dodecylamine, tetradecylamine, decylamine, dioctylamine, didecylamine, dihexylamine, 2-ethyl-1-hexylamine and diisobutylamine.

In some embodiments of the invention that may be mentioned herein, $R_3$ may represent a linear or branched $C_4$-$C_{12}$ (e.g. $C_6$-$C_{10}$) alkyl group.

In some embodiments of the invention that may be mentioned herein, $R_3$ may represent a linear alkyl group.

In some embodiments of the invention that may be mentioned herein, $R_3$ may represent a $C_8$ or $C_{10}$ alkyl group, (e.g. a linear $C_{10}$ alkyl group).

In general, $R_4$ may be selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ (e.g. $C_6$-$C_{10}$) aryl group, and a 5-10 membered heteroaromatic ring system.

In some embodiments of the invention that may be mentioned herein, $R_4$ may be selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{10}$ aryl group, and a 5-10 membered heteroaromatic ring system.

In some embodiments of the invention that may be mentioned herein, $R_4$ may be selected from a phenyl group, a furan group or, more particularly, a linear or branched $C_4$-$C_{18}$ (e.g. $C_4$-$C_{12}$) aliphatic hydrocarbyl group that is saturated or unsaturated.

In some embodiments of the invention that may be mentioned herein, $R_4$ may be selected from a 1,4-valent phenyl group, a 2,5-valent furan group, or more particularly, a linear or branched $C_6$-$C_{10}$ aliphatic hydrocarbyl group that is saturated or unsaturated.

In some embodiments of the invention that may be mentioned herein, $R_4$ may represent a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid.

In some embodiments of the invention that may be mentioned herein, $R_4$ may represent a linear or branched $C_4$-$C_{12}$ (e.g. $C_6$-$C_{10}$) alkylene group.

In some embodiments of the invention that may be mentioned herein, $R_4$ may represent a linear alkylene group.

In some embodiments of the invention that may be mentioned herein, $R_4$ may represent a $C_6$-$C_8$ alkylene group (e.g. a linear $C_7$ alkylene group).

In some embodiments of the invention, the anionic portion is an anionic species of formula Ic:

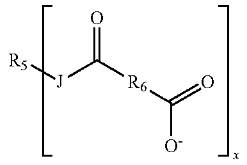

Ic

In general, $R_5$ is selected from the group consisting of a linear, branched or cyclic $C_1$-$C_{20}$ aliphatic hydrocarbyl group that is saturated or unsaturated, a linear or branched $C_2$-$C_{20}$ polyalkyleneglycol group, a $C_6$-$C_{22}$ aryl group, a moiety formed by removing x hydroxyl groups from a sugar alcohol, and a moiety formed by removing x hydroxyl groups from a dehydrated sugar alcohol.

In some embodiments of the invention that may be mentioned herein, $R_5$ may be selected from the group consisting of a linear or branched $C_3$-$C_{14}$ aliphatic hydrocarbyl group that is saturated or unsaturated, a $C_6$-$C_{10}$ aryl group, a moiety formed by removing x hydroxyl groups from a sugar alcohol, and a moiety formed by removing x hydroxyl groups from a dehydrated sugar alcohol.

In some embodiments of the invention that may be mentioned herein, $R_5$ may be selected from the group consisting of a phenyl ring, and a branched $C_3$-$C_{10}$ aliphatic group.

In some embodiments of the invention that may be mentioned herein x may be 3 and $R_5$ may be moiety formed by removing three hydroxyl groups from a compound selected from the group consisting of trimethylolpropane, glycerol, pyrogallol, hydroxyquinol, phloroglucinol, 3-methylpentane-1,3,5-triol.

In some embodiments of the invention that may be mentioned herein x may be 4, and $R_5$ may be a moiety formed by removing four hydroxyl groups from a compound selected from the group consisting of sorbitan, pentaerythritol, di(trimethylolpropane) and di(glycerol).

In some embodiments of the invention that may be mentioned herein x may be 6, and $R_5$ may be a moiety formed by removing six hydroxyl groups from a compound selected from the group consisting of sorbitol, di-pentaerythritol, mannitol, and glucose.

In some embodiments of the invention that may be mentioned herein, $R_5$ may represent a saturated linear or branched $C_2$-$C_8$ (e.g. $C_3$-$C_6$) hydrocarbon linking group.

In some embodiments of the invention that may be mentioned herein, $R_5$ may represent a branched group.

In some embodiments of the invention that may be mentioned herein, $R_5$ may represent a moiety having the formula:

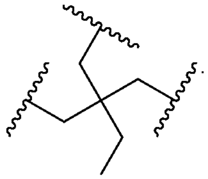 [SMILES: *CC(C*)(C*)CC]

In general, each $R_6$ independently represents a linear, branched or cyclic $C_1$-$C_{20}$ aliphatic hydrocarbyl group that is saturated or unsaturated.

In some embodiments of the invention that may be mentioned herein, each $R_6$ may be independently selected from a phenyl group, a furan group or, more particularly, a linear or branched $C_4$-$C_{18}$ (e.g. $C_4$-$C_{12}$) aliphatic hydrocarbyl group that is saturated or unsaturated.

In some embodiments of the invention that may be mentioned herein, each $R_6$ may be independently selected from a 1,4-valent phenyl group, a 2,5-valent furan group, or more particularly, a linear or branched $C_6$-$C_{10}$ aliphatic hydrocarbyl group that is saturated or unsaturated.

In some embodiments of the invention that may be mentioned herein, each $R_6$ may independently represent a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid.

In some embodiments of the invention that may be mentioned herein, each $R_6$ may independently represent a linear or branched $C_2$-$C_{10}$ (e.g. $C_6$-$C_{10}$) alkylene group.

In some embodiments of the invention that may be mentioned herein, each $R_6$ may independently represent a linear alkylene group.

In some embodiments of the invention that may be mentioned herein, each $R_6$ may independently represent a $C_8$ or $C_{10}$ alkyl group (e.g. a linear $C_8$ alkylene group).

In some embodiments of the invention that may be mentioned herein, x may represent 3. For example, in some embodiments of the invention that may be mentioned herein, the anionic portion may be of formula Ici:

Ici

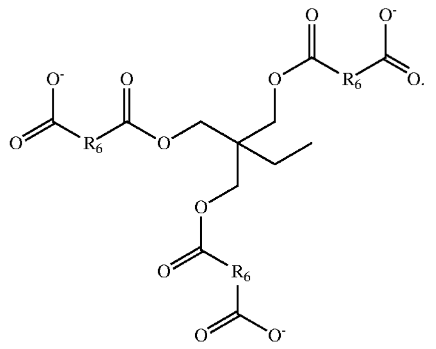

In formula Ici, $R_6$ is as defined here.

In some embodiments of the invention that may be mentioned herein, x may represent 4.

In some embodiments of the invention that may be mentioned herein, x may represent 6.

In some embodiments of the invention that may be mentioned herein, each J may represent O.

In some embodiments of the invention that may be mentioned herein, each J may represent $NR_N$.

In some embodiments of the invention that may be mentioned herein, $R_N$ may represent H or a $C_1$-$C_{10}$ alkyl or alkenyl group. In some embodiments of the invention that may be mentioned herein, $R_N$ may represent oleyl. In some embodiments of the invention that may be mentioned herein, $R_N$ may represent H.

In some embodiments of the invention that may be mentioned herein, $R_2$, $R_3$ or $R_5$, or more particularly $R_1$, $R_4$ or Re, may represent, or be derived from, an alkanolamino group. In other words, the linear or branched $C_1$-$C_{20}$ aliphatic hydrocarbyl group or $C_1$-$C_{40}$ aliphatic hydrocarbyl group (e.g. $C_1$-$C_{40}$ aliphatic hydrocarbyl group) is substituted by one or more (e.g. one, two or three) hydroxyl groups and one or more (e.g. one, two or three) groups selected from the group consisting of primary amino, secondary amino and tertiary amino.

In some embodiments of the invention that may be mentioned herein, $R_2$, $R_3$ or $R_5$, or more particularly $R_1$, $R_4$ or $R_6$, may represent, or be derived from, a polyol ester. In other words, the linear or branched $C_1$-$C_{20}$ aliphatic hydrocarbyl group or $C_1$-$C_{40}$ aliphatic hydrocarbyl group (e.g. $C_1$-$C_{40}$ aliphatic hydrocarbyl group) is interrupted by one or more (e.g. one, two or three) ester groups and/or is substituted by one or more (e.g. one, two or three) hydroxyl groups.

The ionic liquid comprises a cationic portion having formula Ib:

$$(X)_n^{a+} \quad \text{Ib}$$

X represents a cationic species, where a is 1 or 2 and n is 1 or 2, provided that:

when a is 1 then n is 2, and when a is 2 then n is 1.

Thus, a and n are together selected to balance the charge of the anionic portion of the ionic liquid, which is 2−.

In some embodiments of the invention that may be mentioned herein, a may represent 1. In other words, the cationic species X may have a charge of +1. In such embodiments, n may represent 2.

The cationic portion may be selected from any appropriate cationic portion that does not interfere with components in the base oil. In some embodiments of the invention that may be mentioned herein, the cationic portion may be selected from one or more of the group consisting of a quaternary phosphonium cation, a quaternary sulphonium cation, a quaternary ammonium cation comprising at least one amide group, a quaternary ammonium cation comprising at least one ester group, a substituted quaternary imidazolium cation comprising at least one ester group, a substituted quaternary imidazolium cation comprising at least one alkyleneglycol group, a substituted quaternary imidazolium cation comprising at least one amide group, azaannulenium, azathiazolium, benzimidazolium, benzofuranium, benzothiophenium, benzotriazolium, borolium, cinnolinium, diazabicyclodecenium, diazabicyclononenium, 1,4-diazabicyclo [2.2.2]octanium, diazabicyclo-undecenium, dibenzofuranium, dibenzothiophenium, dithiazolium, dithiazolium, furanium, guanidinium, imidazolium, indazolium, indolinium, indolium, morpholinium, oxaborolium, oxaphospholium, oxazinium, oxazolium, iso-oxazolium, oxazolinium, pentazolium oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, isoquinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, combinations thereof, and cationic molecules comprising more than one of the foregoing.

As mentioned above, the cationic portion may represent a species comprising more than one cationic group. For example, the cationic portion may represent a species comprising two cationic groups, each having a charge of 1+.

In some embodiments of the invention that may be mentioned herein, the cationic portion may have the formula $[YX_3X_4X_5X_6]^+$, wherein:

Y represents N, P or S (e.g. N or P).

In such embodiments, each of $X_3$ to $X_6$ may be independently selected from $C_1$ to $C_{30}$ straight chain or branched alkyl and alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$ to $X_6$ combine to form an alkylene chain $—(CH_2)_q—$ wherein q is from 3 to 6; wherein any one or more of said straight or branched chain alkyl and alkenyl groups, cycloalkyl groups, arylalkyl groups, alkylaryl groups; aryl groups or alkylene chains are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl; or Alternatively, in such embodiments at least one of $X_3$ to $X_B$ may have the formula $—X_7O(C{=}O)X_8$ or $—X_7(C{=}O)—O—X_8$, wherein $X_7$ is a $C_1$ to $C_{10}$ straight chain or branched alkyl or alkenyl group, or a $C_3$ to $C_6$ cycloalkyl or cycloalkenyl group; and $X_8$ is a $C_1$ to $C_{30}$ straight chain or branched alkyl or alkenyl group; a $C_3$ to $C_6$ cycloalkyl group; a $C_1$ to $C_{30}$ arylalkyl group; a $C_1$ to $C_{30}$ alkylaryl group; an aryl group; or any two respective $X_8$ groups combine to form an alkylene chain $—(CH_2)_q—$ wherein q is from 3 to 6; wherein $X_7$ and/or $X_8$ are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl; groups, arylalkyl groups, alkylaryl groups; aryl groups or alkylene chains is optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl.

In some embodiments of the invention that may be mentioned herein, each of $X_3$ to $X_6$ may independently represent $C_1$ to $C_{30}$ straight chain or branched alkyl and alkenyl groups, such as $C_1$ to $C_{30}$ straight chain or branched alkyl groups, for example $C_4$ to $C_{18}$ straight chain or branched alkyl groups. In a specific embodiment of the invention that may be mentioned herein, $X_3$ to $X_6$ may independently represent $C_4$ to $C_{18}$ straight chain alkyl groups.

In some embodiments of the invention that may be mentioned herein, $X_3$ to $X_5$ may be the same and $X_6$ may be different to $X_3$ to $X_5$. For example, $X_6$ may represent methyl, and each of $X_3$ to $X_5$ may represent octyl.

In other embodiments of the invention that may be mentioned herein, each of $X_3$ to $X_6$ may be the same. For example, each of $X_3$ to $X_6$ may represent butyl.

In some embodiments of the invention that may be mentioned herein, Y may represent P.

In some embodiments of the invention that may be mentioned herein, the cationic portion may be selected from the group consisting of:

trioctyl methyl ammonium; tetrabutylphosphonium; trioctylmethyl phosphonium; tetraoctyl ammonium; dioctadecyldiammonium; and

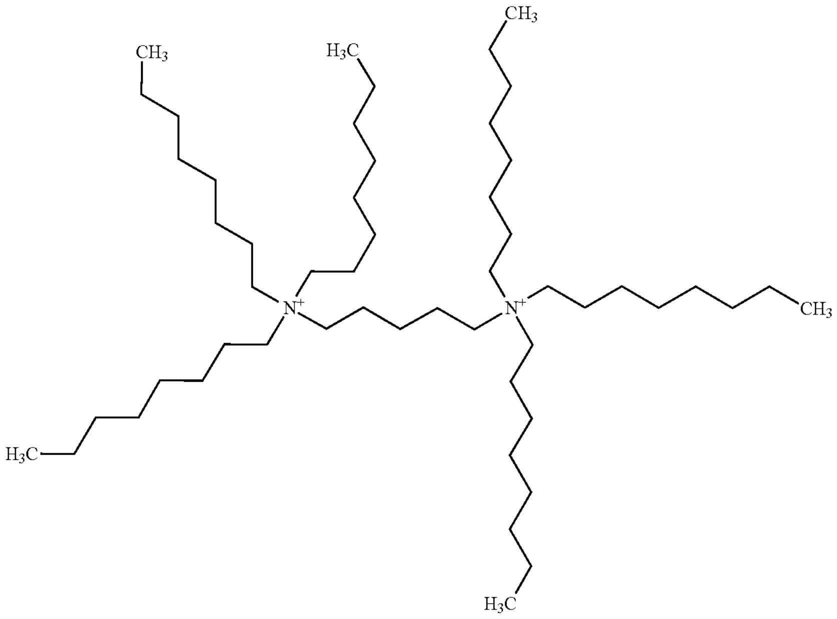 [SMILES: CCCCCCCC[N+](CCCCCCCC)(CCCCCCCC)CCCCC[N+](CCCCCCCC)(CCCCCCCC)CCCCCCCC]

and the other of $X_3$ to $X_6$ that are not as defined above may be independently selected from $C_1$ to $C_{30}$ straight chain or branched alkyl and alkenyl groups such as $C_1$ to $C_{10}$ alkyl or alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$, $X_4$, $X_5$ and $X_6$ combine to form an alkylene chain $—(CH_2)_q—$ wherein q is from 3 to 6; wherein any one or more of said straight or branched chain alkyl and alkenyl groups, cycloalkyl In some embodiments of the invention that may be mentioned herein, the cationic portion may be tetrabutylphosphonium.

In some embodiments of the invention that may be mentioned herein, the cationic portion may be trioctyl methyl ammonium.

The invention also provides a composition comprising:

a base fluid, and an ionic liquid as defined herein.

Examples of suitable base fluids include a base oil; a base fuel; and a solvent.

As used herein a "base oil" refers to an oil comprising one or more base stocks. As used herein, a "base stock" is as defined according to API standard 1509, Appendix E. Typical lubricant base stocks that can be used in this invention may include natural base oils, including mineral oils, petroleum oils, paraffinic oils and vegetable oils, as well as oils derived from synthetic sources. In particular, lubricant base stocks that can be used in this invention may be petroleum-based or synthetic stocks including any fluid that falls into the API base stock classification as Group I, Group II, Group III, Group IV, and Group V. The hydrocarbon base oil may be selected from naphthenic, aromatic, and paraffinic mineral oils.

In some embodiments of the invention, the base oil comprises one or more base stocks selected from Group I base stocks, Group II base stocks, Group III base stocks, Group IV base stocks and Group V base stocks.

In some embodiments of the invention, the base oil comprises one or more synthetic oils selected from polyalpha-olefins, synthetic esters, polyalkylene glycols, phosphate esters, alkylated naphthalenes, silicate esters, ionic fluids, or multiply alkylated cyclopentanes.

Examples of suitable base oils include LB 25, LB 44 and LB 100 disclosed in WO 2014/133380.

The composition may comprise any suitable amount of ionic liquid, for example an amount that is sufficient to provide lubrication to the base oil. In some embodiments of the invention that may be mentioned herein, the composition may comprise from 0.01 to 10 wt. % (e.g. 0.1 to 5 wt. %) ionic liquid.

In some embodiments of the invention, the ionic liquid may have a solubility in the base oil or polyol ester of from 0.1 to 10 wt. %.

The invention also provides the use of an ionic liquid as a friction modifier additive in a base oil or in a polyol ester, wherein the ionic liquid is as defined herein.

The invention also provides a method of reducing the friction of a base oil or polyol ester, said method comprising the steps:

(i) providing a base oil or polyol ester; and
(ii) mixing the base oil or polyol ester with an appropriate amount of an ionic liquid, which ionic liquid is as defined herein.

In the above use and method of the invention, the base oil may comprise a base stock selected from the group consisting of a Group I base stock, a Group II base stock, a Group III base stock, a Group IV base stock, a Group V base stock, and combinations thereof; and the polyol ester may comprise a mixture of polyol esters.

The invention also provides method of preparing an ionic liquid as defined herein, said method comprising the steps:

(i) providing an intermediate product comprising:
  an ester group or an amide group; and
  a carboxylic acid group;
(ii) converting the intermediate product to an ionic liquid by either:
  (a) directly reacting the intermediate product with a cationic base;
  (b) deprotonating the intermediate esters with a base to form an ester alkaline/metal salts, subsequently conducting a metathesis reaction between the ester salt with a salt compound that comprises a cationic portion having formula A; or
  (c) reacting the intermediate product with an alkylamine or arylamine.

In some embodiments of the invention that may be mentioned herein, the alkylamine may be selected from the group consisting of:

$C_1$-$C_{20}$ alkyl-mono alkyl amines that are saturated or unsaturated (e.g. oleyl amine, decylamine, tetradecyl amines);

$C_1$-$C_{20}$ alkyl-dialkyl amines that are saturated or unsaturated, (e.g. diisopropylamine, dioctyl amine, dioleylamine, diphenyl amine); and $C_1$-$C_{20}$ alkyl-trialkyl amines that are saturated or unsaturated, (e.g. N,N-dimethyl octyl amine, N,N-dimethyl phenyl amine).

In some embodiments of the invention that may be mentioned herein, the ester group or amide group may be an ester group.

In some embodiments of the invention that may be mentioned herein, the intermediate product may be provided by reacting an alcohol or amine with a dicarboxylic acid to produce said intermediate product. In some embodiments of the invention that may be mentioned herein, the alcohol or amine may be an alcohol.

In some embodiments of the invention that may be mentioned herein, the cationic base may be selected from the group consisting of a tetraalkyl ammonium hydroxide, a tetraalkyl phosphonium hydroxide, a tetraalkyl ammonium methylcarbonate, and a tetraalkyl phosphonium methylcarbonate.

In some embodiments of the invention that may be mentioned herein, the base may be selected from the group consisting of LiOH, NaOH, $NaHCO_3$ and KOH.

In the above method of the invention, the alcohol may have any appropriate number of hydroxyl groups. For example, the alcohol may be selected from the group consisting of a mono-alcohol, a diol and a triol.

In some embodiments of the invention that may be mentioned herein, the method may comprise:

reacting an alcohol with a dicarboxylic acid to produce the intermediate product; and a preliminary step of choosing the alcohol and dicarboxylic acid based on a desired polarity of the ionic liquid.

For example, the alcohol and dicarboxylic acid may be chosen to provide an ionic liquid having a desired solubility in a base oil or polyol ester. A desired solubility of ionic liquid in the base oil or polyol ester may be from 0.1 to 10 wt. %.

The invention also provides a salt comprising:

an anionic portion as defined herein, and a cationic portion comprising one or more alkali metal cations (e.g. Li, $Na^+$ or $K^+$).

The invention also provides a method of preparing a salt as defined herein, said method comprising the steps:

i) reacting an alcohol with a dicarboxylic acid to produce an intermediate product comprising an ester group and a carboxylic acid group;

(ii) reacting the intermediate product with a basic salt of an alkali metal (e.g. a basic lithium, sodium or potassium salt, such as LiOH, NaOH, $NaHCO_3$ or KOH) to form a salt as defined herein.

The invention is illustrated by the below Examples, which are not to be construed as limitative.

EXAMPLES

Starting materials for ionic liquid synthesis were purchased from Sigma-Aldrich.

Example 1: Synthesis of 5B-DC12 and 5B-DC10

5B-DC12:

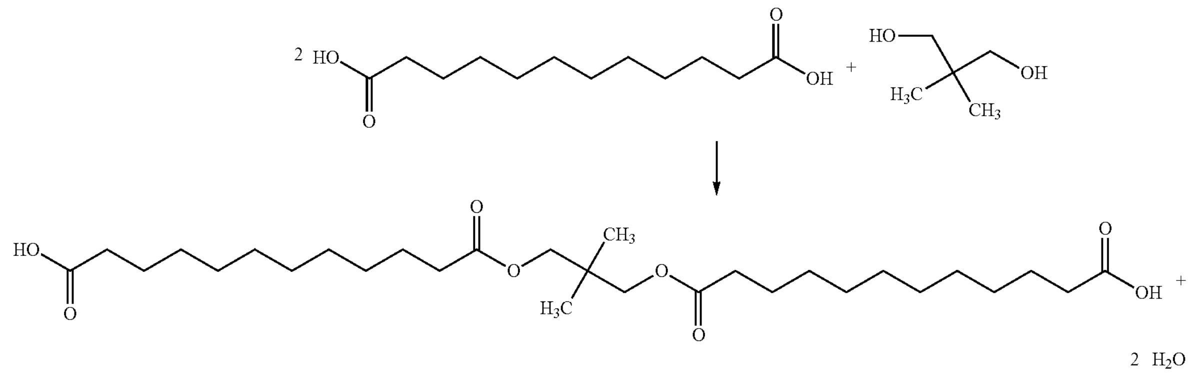

110 g (0.4728 mol) of dodecanedioic acid (99% purity) and 24.87 g (0.2364 mol) of neopentyl glycol (99% purity) were mixed in a round bottom flask fitted with a gas inlet tube for nitrogen gas blanketing, with magnetic bar on a magnetic stirrer, a distillation column fitted with a cooled condenser and collection flask to collect distilled water by-product. The mixture was initially homogenized at 100° C. using mechanical stirring, followed by gradual temperature increase to 180° C. and subsequently to 210° C. over 5 hours. In order to drive the esterification to near completion, nitrogen gas was sparged into the reaction mixture at a rate of 0.5 SCFH. The reaction was deemed complete when no more water distilled water was collected. Upon cooling, a white waxy solid product was obtained (5B-DC12). The esters were characterised by $^{1}H$ NMR, $^{13}C$ NMR and FT-IR to confirm the formed structure.

5B-DC12 (neopentylglycol didodecanedioate), $C_{29}H_{52}O_8$:

$^{1}H$ NMR ($CD_3OD$, 400 MHz): δ (ppm) 3.87 (s, 4H), 2.32 (m, 4H, J=8.0 Hz), 2.26 (m, 4H, J=8.0 Hz), 1.58 (m, 8H, J=8.0 Hz), 1.30 (m, 24H), 0.97 (s, 6H).

$^{13}C\{^{1}H\}$ NMR ($CD_3OD$, 101 MHz): δ (ppm) 176.33, 173.87, 68.66, 34.33, 33.57, 29.12, 28.97, 24.70, 20.68

FT-IR ($cm^{-1}$): 3031.97, 2918.77, 2850.82, 1735.73, 1694.62, 1466.89, 1431.89, 1383.90, 1279.85, 1221.84, 1167.75, 1002.92, 931.58, 723.69, 683.19.

5B-DC10:

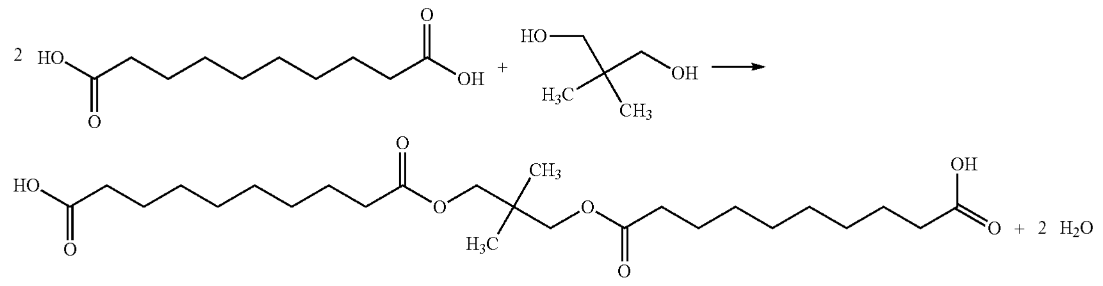

108 g (0.529 mol) of sebacic acid (99% purity) and 27.55 g (0.2645 mol) of neopentyl glycol (99% purity) were mixed in a round bottom flask fitted with a gas inlet tube for nitrogen gas blanketing, with magnetic bar on a magnetic stirrer, a distillation column fitted with a cooled condenser and collection flask to collect distilled water by-product. The mixture was initially homogenized at 100° C. using mechanical stirring, followed by gradual temperature increase to 180° C. and subsequently to 210° C. over 5 hours. In order to drive the esterification to near completion, nitrogen gas was sparged into the reaction mixture at a rate of 0.5 SCFH. The reaction was deemed complete when no more water distilled water was collected. Upon cooling, a white waxy solid product was obtained (5B-DC10). The esters were characterised by $^{1}H$ NMR, $^{13}C$ NMR and FT-IR to confirm the formed structure.

5B-DC10 (Neopentylglycol Disebacate), $C_{25}H_{44}O_8$:

$^{1}H$ NMR ($CDCl_3$, 400 MHz): δ (ppm) 3.88 (s, 4H), 2.33 (m, 8H, J=8.0 Hz), 1.61 (m, 8H, J=8.0 Hz), 1.31 (m, 16H), 0.96 (s, 6H).

$^{13}C\{^{1}H\}$ NMR ($CDCl_3$, 101 MHz): δ (ppm) 179.78, 173.77, 69.05, 34.64, 34.26, 33.99, 29.09, 28.91, 24.92, 21.76

FT-IR ($cm^{-1}$): 3031.97, 2933.65, 2852.76, 1738.44, 1701.48, 1470.79, 1303.77, 1242.73, 1178.69, 1005.87, 932.98, 724.39, 680.49.

Example 2: Formation of Ionic Liquids ILN18-5B-DC12 and ILP4-5B-DC10

ILN18-5B-DC12

In a round bottom flask, 4.1825 g (7.911 mmol) of synthesised 5B-DC12 (Example 1) was dissolved in 50 mL of ethanol. 4.1825 g (7.911 mmol) of trioctyl methyl ammonium methyl carbonate (50%) solution was charged into an addition funnel attached to the flask containing the ester solution, then the cation solution was slowly added at about 1 drop per second until completion. The mixture was stirred uninterrupted at room temperature overnight, followed by 2 h stirring at 50° C. The reaction formed methanol and $CO_2$ as by-products, which were removed by rotary evaporation along with the ethanol solvent. The ionic liquid was further purified by high vacuum Schlenk-line drying overnight, resulting into an amber viscous liquid end product at 99% yield.

The ionic liquid ILN18-5B-DC12 comprised:

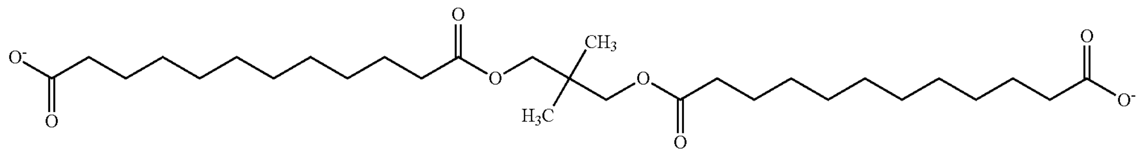 [SMILES: CC(C)(COC(=O)CCCCCCCCCCC(=O)[O-])COC(=O)CCCCCCCCCCC(=O)[O-]]

as the anionic portion (1 equivalent); and trioctyl methyl ammonium (2 equivalents) as the cationic portion.

The product was confirmed by $^1$H NMR, $^{13}$C NMR and FT-IR spectroscopy.

The ashless nature of the formed ionic liquid was confirmed by thermo-gravimetric analysis under nitrogen (0.4788 wt. % residue).

ILN18-5B-DC12 (bis-(trioctyl methylammonium) didodecanedioate), $C_{79}H_{158}N_2O_8$:

$^1$H NMR ($CD_3OD$, 400 MHz): δ (ppm) 3.91 (s, 4H), 3.25 (m, 12H, J=4.0 Hz), 3.00 (s, 6H), 2.33 (m, 4H, J=4.0 Hz), 2.16 (m, 4H, J=4.0 Hz), 1.71 (m, 12H), 1.59 (m, 8H), 1.35 (m, 84H), 0.98 (s, 6H), 0.91 (m, 18H).

$^{13}$C{$^1$H} NMR ($CD_3OD$, 101 MHz): δ (ppm) 182.87, 175.89, 70.44, 63.10, 39.39, 36.11, 35.42, 33.23, 30.55, 27.76, 26.50, 24.04, 23.51, 22.41, 14.76

FT-IR (cm$^{-1}$): 2923.64, 2854.74, 1735.82, 1578.55, 1466.80, 1376.72, 1251.89, 1175.86, 1073.89, 901.89, 732.88, 629.80, 586.40, 473.59.

ILP4-5B-DC10

In a single neck round bottom flask equipped with a magnetic stirrer, 0.9963 g (2.02 mmol) of 5B-DC10 (Example 1) was dissolved in 10 mL of ethanol. The mixture was stirred until solution was clear. In an addition funnel, 2.7973 g of tetrabutyl phosphonium hydroxide [P4444][OH] (4.04 mmol, 40% purity) was charged, and 10 mL of ethanol was added with stirring. The solution was then attached to the round bottom flask and the base was slowly dropped into the solution. Once done, the mixture was stirred for about 2 h before high vacuum distillation to dry off the solvent and water. The final product, which was a clear viscous liquid was collected with the product yield of 98%, characterised by $^1$H NMR, $^{13}$C NMR, $^{31}$P NMR and FT-IR.

ILP4-5B-DC10 (bis-(tetrabutyl phosphonium) disebacate), $C_{57}H_{114}O_8P_2$:

$^1$H NMR ($CDCl_3$, 400 MHz): δ (ppm) 3.85 (s, 4H), 2.45 (m, 16H, J=12.0 Hz), 2.27 (m, 4H, J=4.0 Hz), 2.13 (m, 4H, J=4.0 Hz), 1.58 (m, 8H), 1.49 (m, 32H), 1.26 (m, 16H), 0.94 (m, 30H).

$^{13}$C{$^1$H} NMR ($CDCl_3$, 101 MHz): δ (ppm) 178.41, 172.82, 68.06, 38.91, 33.67, 33.35, 29.49, 28.58, 28.25, 28.09, 24.06, 23.13, 22.97, 17.95, 17.48, 12.52.

$^{31}$P NMR ($CDCl_3$, 162 MHz) δ (ppm) 33.15.

FT-IR (cm$^{-1}$): 2928.81, 2858.87, 1734.70, 1574.57, 1464.85, 1373.72, 1302.92, 1238.88, 1097.86, 1003.92, 908.69, 815.59, 723.88.

The ionic liquid ILP4-5B-DC10 comprised:

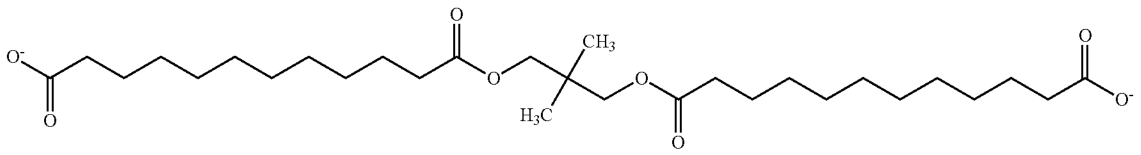 [SMILES: CC(C)(COC(=O)CCCCCCCCCCC(=O)[O-])COC(=O)CCCCCCCCCCC(=O)[O-]]

as the anionic portion (1 equivalent); and tetrabutyl phosphonium (2 equivalents) as the cationic portion.

Example 3: ILN18-5B-DC12 in Lubricant Base Oils

ILN18-5B-DC12 was mixed in mineral base oil Group III+ (ETRO 4+) and PETRONAS LB 25 polyol ester (and their mixtures) at 1 wt. % concentration to assess solubility and tribology evaluation. Samples were prepared by mixing the solutions at 60° C. for 1 h.

Experimental Solubility

| Formulation 1 | Formulation 2 | Formulation 3 |
|---|---|---|
| 1 wt % in Group III Mineral Oil (ETRO 4+) Insoluble | 1 wt % in PETRONAS polyol ester LB 25 Soluble, clear solution | 1 wt % in ETRO 4+ (89%) and LB 25 (10%) Soluble, clear solution |

Computer-Modelled Solubility

Liquid-liquid equilibrium (LLE) was calculated by COSMOtherm software in non-polar medium.

Calculated stable solubility of neutral and resultant IL compounds based on LLE point in non-polar model base oil (n-hexadecane), concentration by mass fraction (g/g), level of parameterization=TZVP-fine, at 2 different temperatures (25° C. and 60° C.). The LLE point in mass fraction (g/g) at 25° C. was $2.5107\times10^{-19}$, while the LLE point in mass fraction (g/g) at 60° C. was $3.157\times10^{-17}$.

ILN18-5B-DC12 was insoluble in non-polar base oils, but soluble in polyol esters.

Tribology Evaluation

High Frequency Reciprocating Rig (HFRR): tribology test rubbing of ball to disc metal specimens, under pure sliding contact (boundary lubrication regime), load at 400 g, frequency at 20 Hz, temperature at 120° C. for 60 mins. Only visually soluble solutions were evaluated, therefore, only Formulation 2 and Formulation 3 were tested. Reported values were the average of minimum 2 repeat runs.

Results for 1 wt % ILN18-5B-DC12 in Polar Polyol Ester Base Oil, PETRONAS LB25:

Friction coefficient behaviour over contact time is shown in FIG. 1. The results show a significant friction reduction for polyol ester with 1 wt % ILN18-5B-DC12 compared to the baseline fluid.

Figure 2:
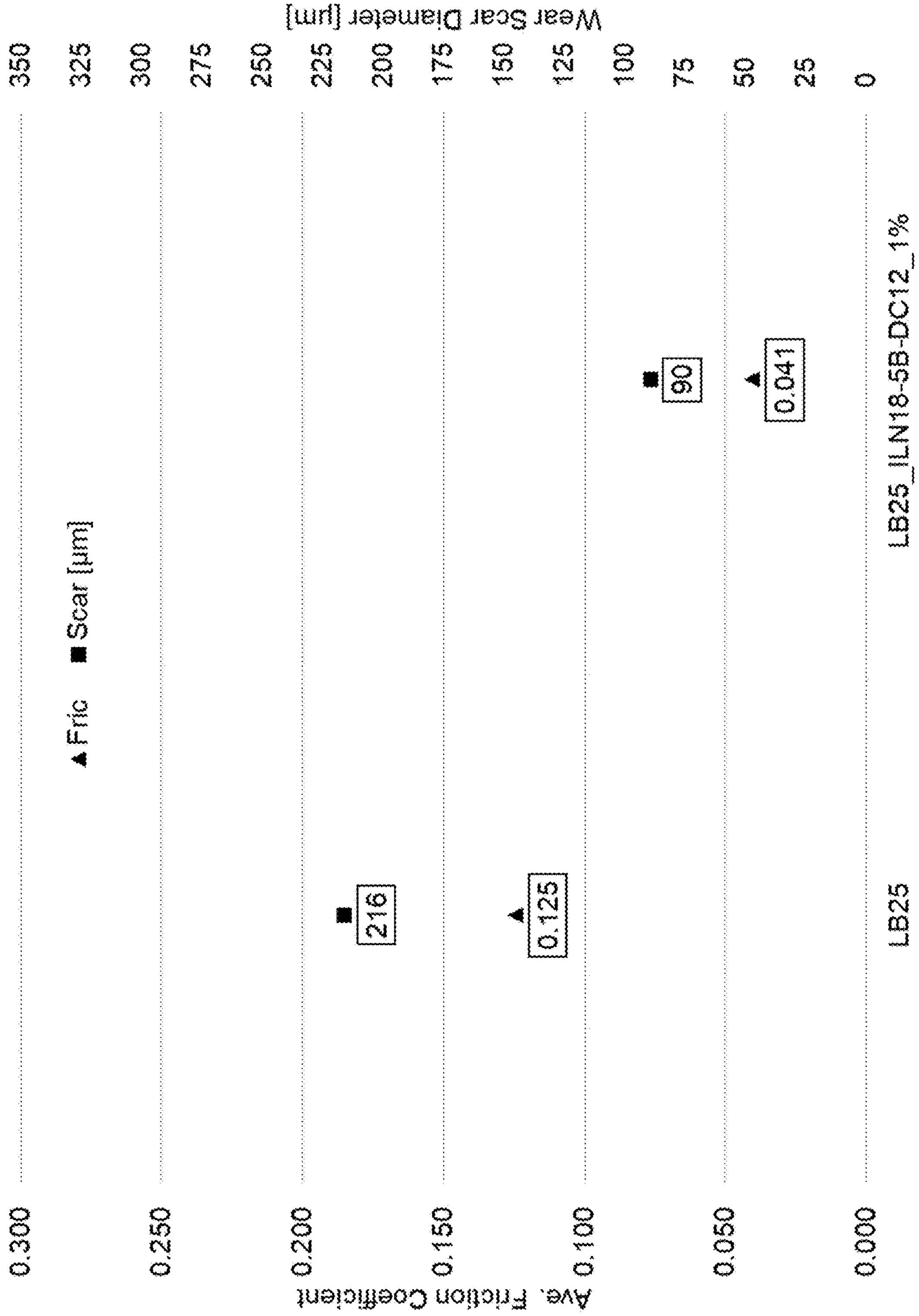
FIG. 2 shows friction coefficient average and measured scar wear diameter average for an ionic liquid according to the invention (ILN18-5B-DC12) in a polar polyol ester base oil (Petronas LB 25).

Friction coefficient average and measured wear scar diameter average from HFRR is shown in FIG. 2. The results show a 67% friction reduction and 59% wear scar diameter reduction compared to the baseline fluid.

Figure 3:
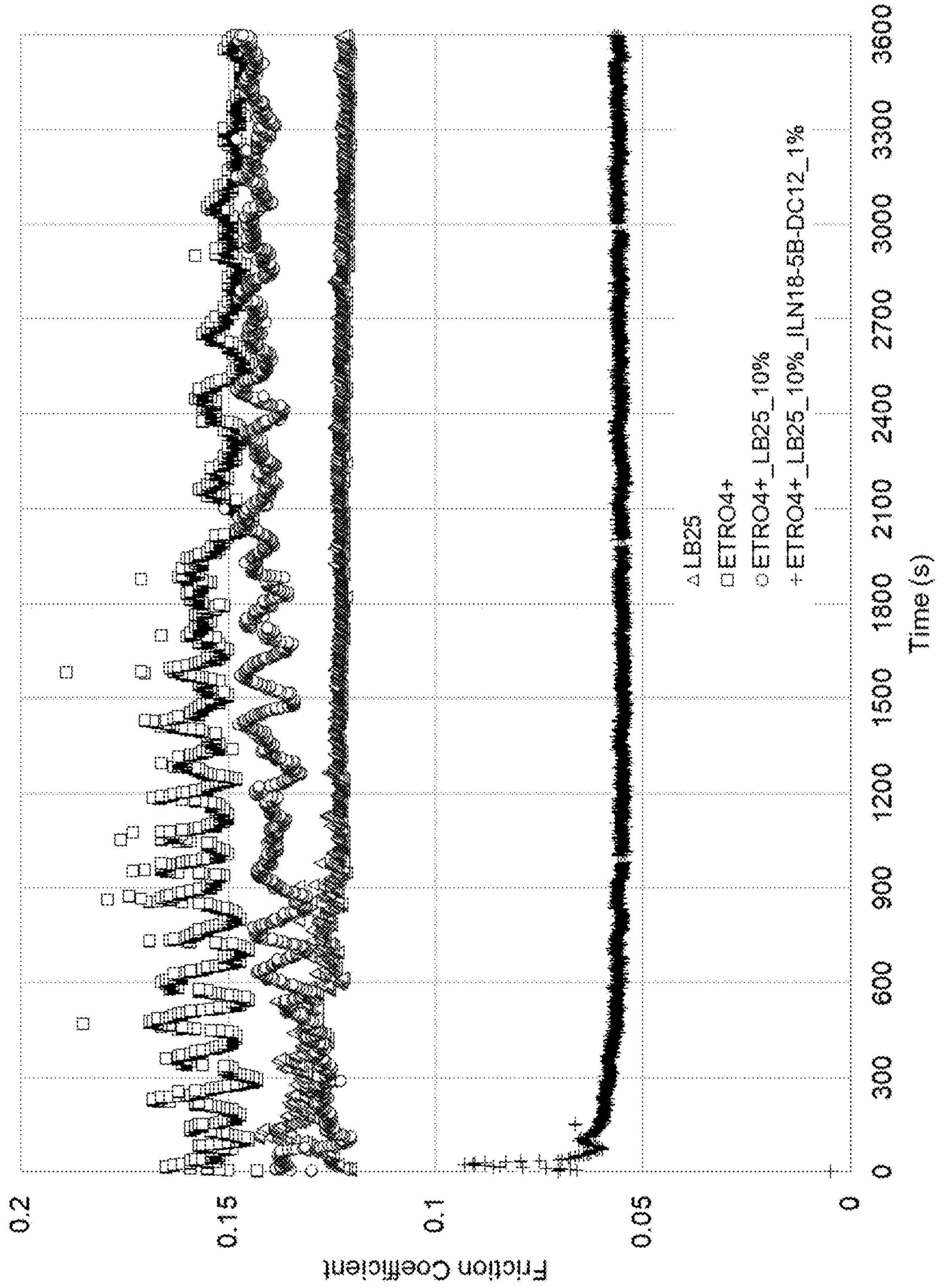
FIG. 3 shows friction coefficient behaviour for an ionic liquid according to the invention (ILN18-5B-DC12) in a mixture of non-polar base oil (ETRO 4+) and polar polyol ester base oil (Petronas LB 25).

Results for 1 wt % ILN18-5B-DC12 in ETRO 4+(89%) and LB 25 (10%):

Friction coefficient behaviour over contact time is shown in FIG. 3. The results show a significant friction reduction behaviour observed for oil containing 89% non-polar base oil (Group III+ base oil, ETRO 4+) with 10% LB 25 polyol ester added with 1 wt % ILN18-5B-DC12.

Figure 4:
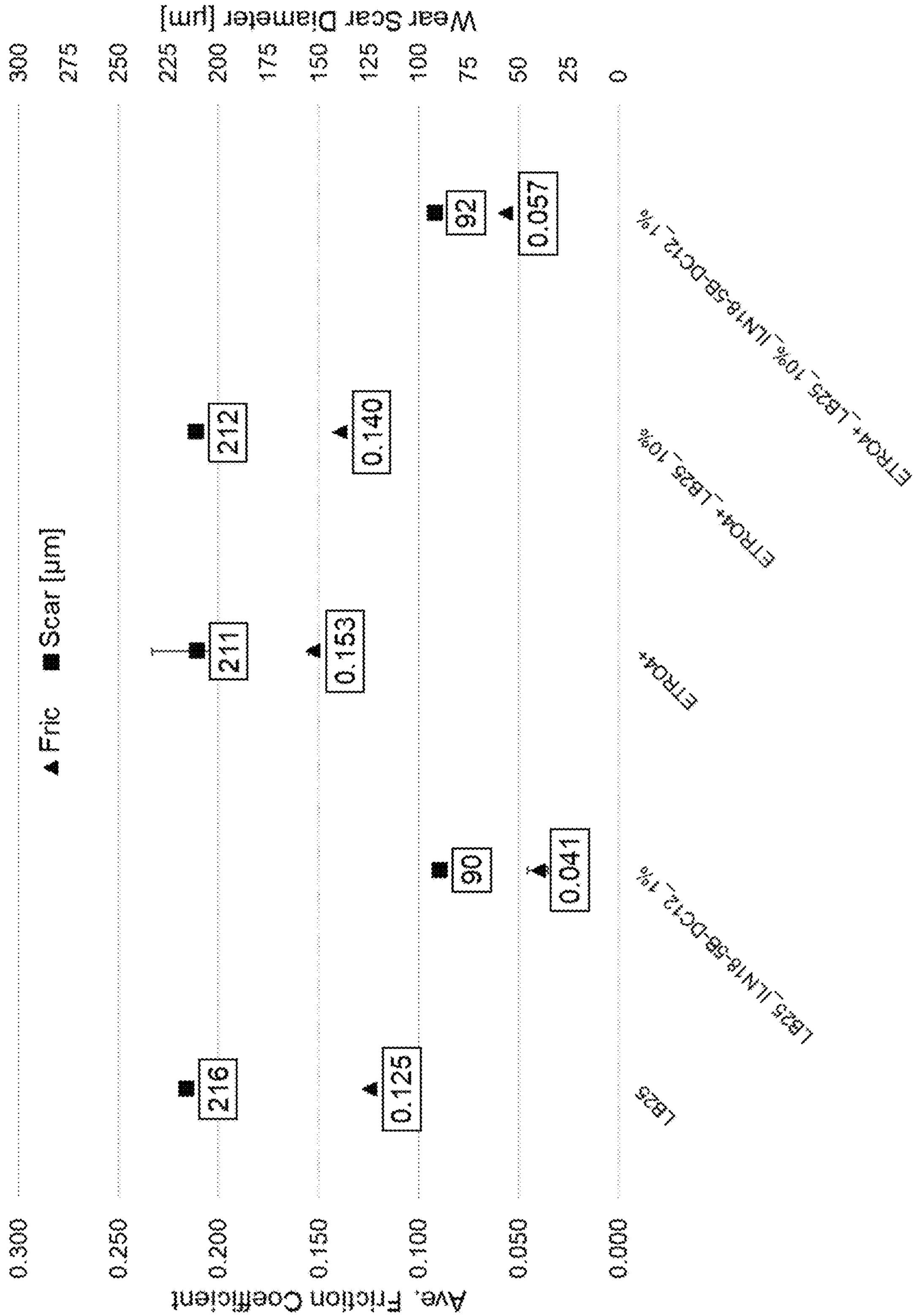
FIG. 4 shows friction coefficient average and measured scar wear diameter average for an ionic liquid according to the invention (ILN18-5B-DC12) in a mixture of non-polar base oil (ETRO 4+) and polar polyol ester base oil (Petronas LB 25).

Friction coefficient average and measured wear scar diameter average from HFRR is shown in FIG. 4. The results show a 55% friction reduction and 57% wear scar diameter reduction compared to baseline as demonstrated by 1 wt % of ILN18-5B-DC12 in oil containing 89% non-polar base oil (Group III+ base oil, ETRO 4+) with 10% LB 25 polyol ester.

Example 4: Synthesis of 6BT-DC10

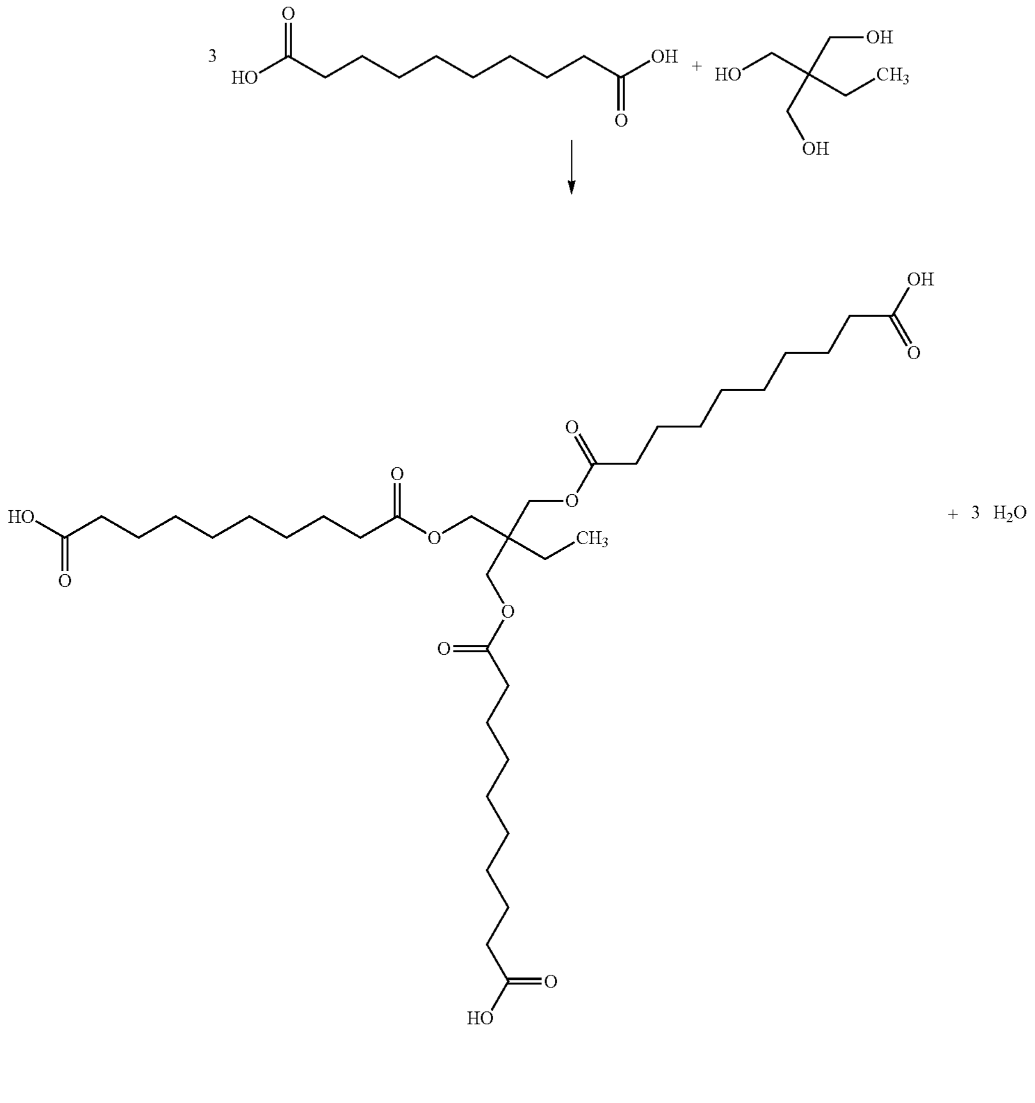

110.42 g (0.546 mol) of sebacic acid (99% purity) and 24.42 g (0.182 mol) of trimethylolpropane alcohol (99% purity) were mixed in a round bottom flask fitted with a gas inlet tube for nitrogen gas blanketing, with magnetic bar on a magnetic stirrer, a distillation column fitted with a cooled condenser and collection flask to collect distilled water by-product. The mixture was initially homogenized at 100° C. using mechanical stirring, followed by gradual temperature increase to 180° C. and subsequently to 210° C. In order to drive the esterification to near completion, nitrogen gas was sparged into the reaction mixture at a rate of 0.5 SCFH. The reaction was deemed complete when no more water distilled water was collected. Upon cooling, a white waxy solid product was obtained (6BT-DC10). The esters were characterised by $^1$H NMR, $^{13}$C NMR and FT-IR to confirm the formed structure.

6BT-DC10 (Trimethylolpropane Trisebacate), $C_{36}H_{62}O_{12}$:

$^1$H NMR ($CD_3OD$, 400 MHz): δ (ppm) 3.97 (s, 6H), 2.32 (m, 6H, J=8.0 Hz), 2.25 (m, 6H, J=8.0 Hz), 1.72 (m, 6H, J=4.0 Hz), 1.60 (m, 6H, J=8.0 Hz), 1.35 (m, 26H), 0.87 (t, 3H, J=8.0 Hz).

$^{13}$C{$^1$H} NMR ($CD_3OD$, 101 MHz): δ (ppm) 179.48, 173.74, 64.28, 40.90, 34.20, 33.92, 29.19, 25.40, 24.78, 22.34, 7.62

FT-IR ($cm^{-1}$): 3041.91, 2933.67, 2852.77, 1741.47, 1700.46, 1467.78, 1300.76, 1242.73, 1187.70, 1002.90, 930.28, 724.58, 680.19, 607.59, 552.29

Example 5: Synthesis of Ionic Liquid ILN18-6BT-DC10

In a round bottom flask, 3.837 g (5.59 mmol) of 6BT-DC10 ester was dissolved in 50 mL of ethanol. 14.875 g (16.76 mmol) of trioctyl methyl ammonium methyl carbonate (50%) solution was charged into an addition funnel attached to the flask containing the ester solution, then the cation solution was slowly added at 1 drop per second rate until completion. The mixture was stirred uninterrupted at room temperature overnight, followed by 2 h stirring at 50° C. The formed methanol and ethanol solvent were removed by rotary evaporator vacuum distillation followed by high vacuum Schlenk-line drying overnight to remove final traces of solvent, resulting into an amber viscous liquid end product at 98% yield.

The product was confirmed by $^1$H NMR, $^{13}$C NMR and FT-IR spectroscopy.

ILN18-6BT-DC10 (tris-(trioctyl methylammonium) trisebacate), $C_{111}H_{221}N_3O_{12}$:

$^1$H NMR ($CD_3OD$, 400 MHz): δ (ppm) 3.99 (s, 6H), 3.31 (m, 18H, J=8.0 Hz), 3.00 (s, 9H), 2.33 (m, 6H, J=8.0 Hz), 2.15 (m, 6H, J=8.0 Hz), 1.71 (m, 18H, J=8.0 Hz), 1.59 (m, 6H, J=8.0 Hz) 1.27 (m, 122H), 0.87 (m, 30H).

$^{13}$C{$^1$H} NMR ($CD_3OD$, 101 MHz): δ (ppm) 183.29, 173.97, 65.46, 61.52, 45.32, 40.90, 38.31, 34.20, 31.42, 30.45, 29.20, 28.58, 28.33, 26.24, 23.63, 23.03, 14.05, 7.63

FT-IR ($cm^{-1}$): 3163.97, 2924.66, 2855.75, 1734.83, 1578.57, 1466.80, 1377.73, 1254.90, 1178.76, 1076.90, 904.49, 723.86, 474.30.

The ashless nature of the formed ionic liquid was confirmed by thermo-gravimetric analysis under nitrogen (0.47271 wt. % residue).

Example 6: ILN18-6BT-DC10 in Lubricant Base Oils

ILN18-6BT-DC10 was mixed in mineral base oil Group III+(ETRO 4+) and PETRONAS LB 25 polyol ester at 1 wt % concentration to assess solubility and tribology evaluation. Samples were prepared by mixing the solutions at 60° C. for 1 h.

Experimental Solubility

| Formulation 1 | Formulation 2 | Formulation 3 |
|---|---|---|
| 1 wt % in Group III Mineral Oil (ETRO 4+) Insoluble | 1 wt % in PETRONAS polyol ester LB 25 Soluble, clear solution | 1 wt % in ETRO 4+ (89%) and LB 25 (10%) Insoluble |

Tribology Evaluation

High Frequency Reciprocating Rig (HFRR): tribology test rubbing of ball to disc metal specimens, under pure sliding contact (boundary lubrication regime), load at 400 g, frequency at 20 Hz, temperature at 120° C. for 60 mins. Only visually soluble solutions were evaluated, therefore, only Formulation 2 was tested. Reported values were the average of minimum 2 replicate runs.

Figure 5:
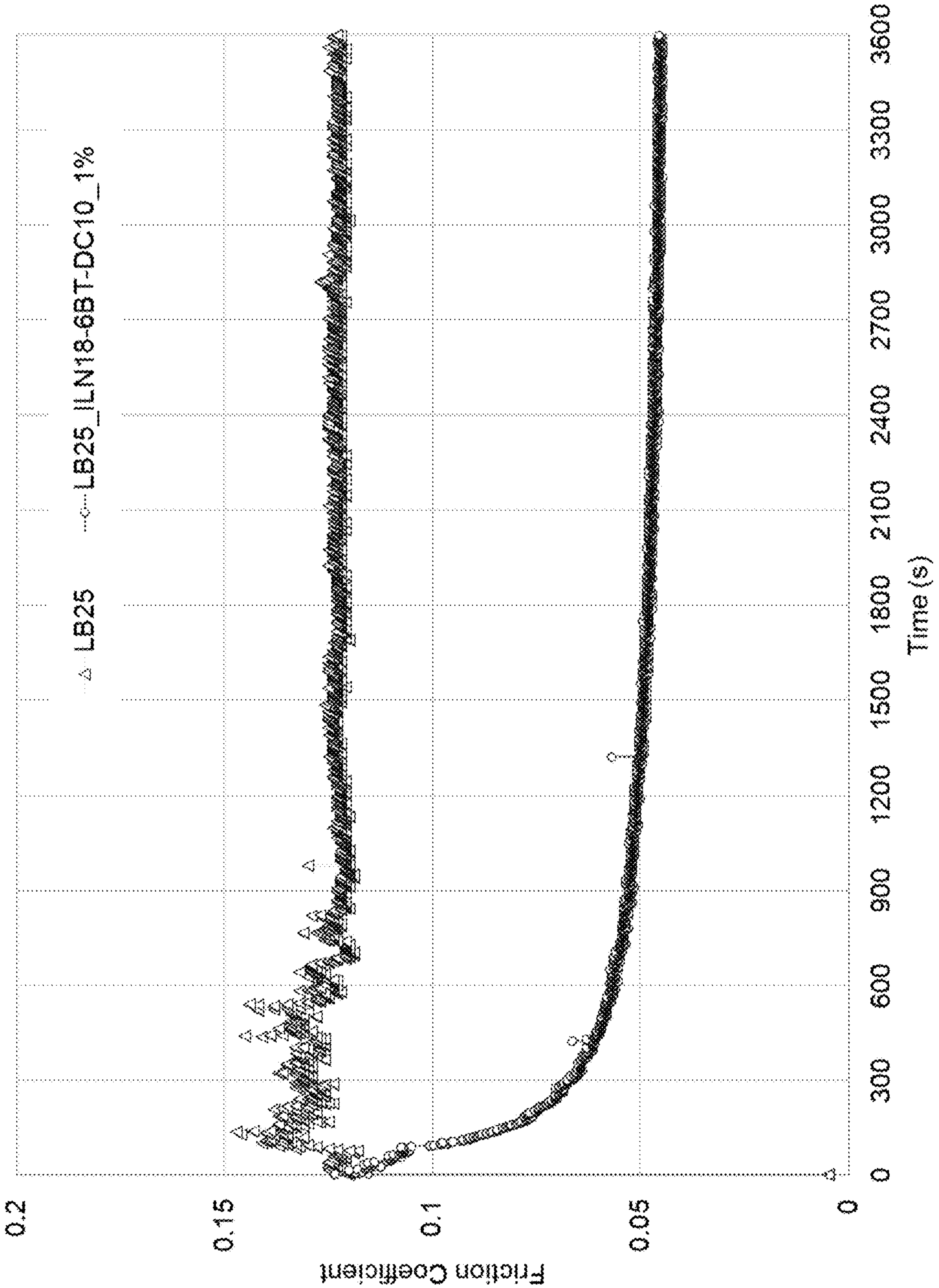
FIG. 5 shows friction coefficient behaviour for an ionic liquid according to the invention (ILN18-6BT-DC10) in a mixture of non-polar base oil (ETRO 4+) and polar polyol ester base oil (Petronas LB 25).

Results for 1 wt % ILN18-6BT-DC10 in 1 wt % in PETRONAS Polyol Ester LB 25:

Friction coefficient behaviour over contact time is shown in FIG. 5. The results show a significant friction reduction in oil containing 1 wt % ILN18-6BT-DC10 compared to the base oil (PETRONAS LB 25).

Figure 6:
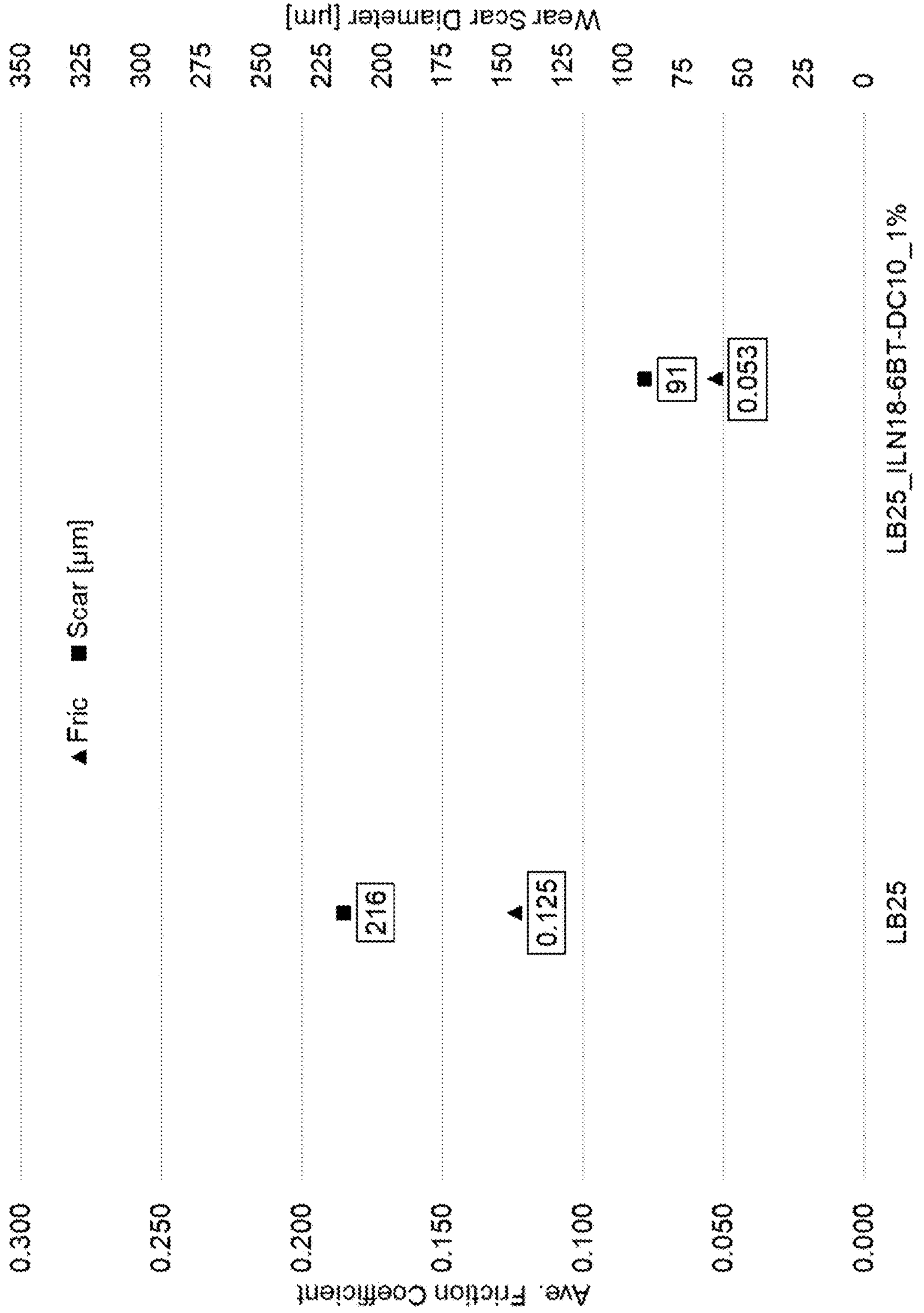
FIG. 6 shows friction coefficient average and measured scar wear diameter average for an ionic liquid according to the invention (ILN18-6BT-DC10) in a mixture of non-polar base oil (ETRO 4+) and polar polyol ester base oil (Petronas LB 25).

Friction coefficient average and measured wear scar diameter average from HFRR is shown in FIG. 6. The results show a 57% friction reduction and 58% wear scar diameter reduction compared to the baseline fluid.

Example 7: Synthesis of Decanoyl Azelate

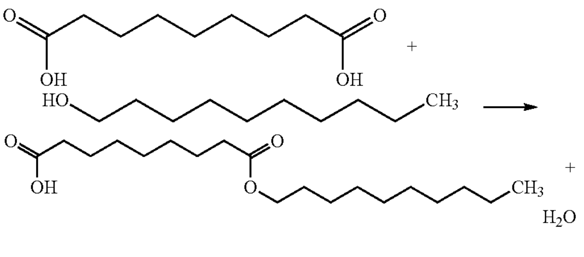

6.3577 g (0.0304 mol) of azelaic acid (90% purity) and 2.455 g (0.0152 mol) of decane-1-ol (98% purity) were mixed in a round bottom flask fitted with a gas inlet tube for nitrogen gas blanketing, with magnetic bar on a magnetic stirrer, a distillation column fitted with a cooled condenser and collection flask to collect distilled water by-product. The mixture was initially homogenized at 100° C. using mechanical stirring, followed by gradual temperature increase to 180° C. and subsequently to 210° C. In order to drive the esterification to near completion, nitrogen gas was sparged into the reaction mixture at a rate of 0.5 SCFH. The reaction was deemed complete when no more water distilled water was collected. The synthesised esters were isolated from the excess acids by dissolving the esters into n-hexane to crash out unreacted azelaic acid, which was then filtered and removed. The filtrate was dried by vacuum distillation to obtain white solids of decanoyl azelate. The purified esters were characterised by $^{1}H$ NMR, $^{13}C$ NMR and FT-IR to confirm the formed structure.

Decanoyl Azelate, $C_{19}H_{36}O_4$:

$^{1}H$ NMR ($CDCl_3$, 400 MHz): δ (ppm) 4.06 (t, 2H, J=8.0 Hz), 2.33 (m, 4H, J=4.0 Hz), 1.62 (m, 6H, J=4.0 Hz), 1.27 (m, 20H), 0.96 (m, 3H).

$^{13}C\{^{1}H\}$ NMR ($CDCl_3$, 101 MHz): δ (ppm) 179.37, 173.97, 64.46, 34.32, 31.88, 29.51, 29.29, 29.23, 25.91, 22.86, 14.10

FT-IR ($cm^{-1}$): 2924.64, 2855.74, 1737.83, 1579.59, 1466.81, 1377.76, 1303.91, 1242.91, 1173.86, 1083.93, 983.29, 902.49, 723.49, 598.49, 511.80, 472.60

Example 9: ILN18-MECA 1 in Lubricant Base Oils

ILN18-MECA-1 was mixed in mineral base oil Group III+(ETRO 4+) and PETRONAS LB 25 polyol ester at 1 wt % concentration respectively to assess solubility and tribology evaluation. Samples were prepared by mixing the solutions at 60° C. for 1 h.

Experimental Solubility

| Formulation 1 | Formulation 2 | Formulation 3 |
|---|---|---|
| 1 wt % in Group III Mineral Oil (ETRO 4+)<br>Soluble (slightly hazy but stable) | 1 wt % in PETRONAS polyol ester LB 25<br>Soluble, clear solution | 1 wt % in ETRO 4+ (89%) and LB 25 (10%)<br>Soluble, clear solution |

FT-IR ($cm^{-1}$): 3040.96, 2920.63, 2852.72, 1728.60, 1691.48, 1467.81, 1361.90, 1314.77, 1237.74, 1177.59, 1097.91, 1054.92, 1012.94, 922.18, 772.95, 724.18, 680.79, 528.90, 428.19

Example 8: Synthesis of ILN18-MECA 1

In a round bottom flask, 0.9437 g (2.873 mmol) of decanoyl azelate was dissolved in 30 mL ethanol. 2.5496 g (2.873 mmol) of trioctyl methyl ammonium methyl carbonate (50%) solution was charged into a dropping funnel and which then attached to the flask containing the ester solution, then slowly adding the cation solution at about 1 drop per second until completion. The mixture was stirred uninterrupted at room temperature overnight, followed by 2 h stirring at 50° C. The formed methanol and ethanol solvent were removed by rotary evaporator vacuum distillation followed by high vacuum Schlenk-line drying overnight, resulting into an amber viscous liquid end product at 99% yield.

The ionic liquid ILN18-MECA 1 comprised:

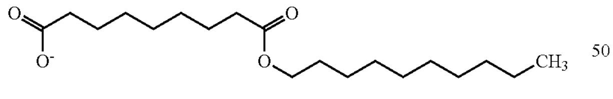

as the anionic portion; and trioctyl methyl ammonium as the cationic portion (1:1).

The product was confirmed by $^{1}H$, $^{13}C$ NMR and FT-IR spectroscopy.

ILN18-MECA-1 Trioctyl Methylammonium Decanoyl Azelate, $C_{44}H_{89}NO_4$:

$^{1}H$ NMR ($CDCl_3$, 400 MHz): δ (ppm) 4.04 (m, 2H), 3.43 (m, 6H, J=8.0 Hz), 3.32 (s, 3H), 2.27 (m, 2H, J=8.0 Hz), 2.16 (m, 2H, J=4.0 Hz), 1.61 (m, 12H, J=8.0 Hz), 1.26 (m, 50H, J=16.0 Hz), 0.88 (m, 12H, J=8.0 Hz).

$^{13}C\{^{1}H\}$ NMR ($CDCl_3$, 101 MHz): δ (ppm) 179.48, 174.03, 64.28, 61.07, 48.58, 39.13, 34.41, 31.58, 28.96, 26.30, 25.86, 22.51, 13.98

Computer-Modelled Solubility

Liquid-liquid equilibrium (LLE) was calculated by COSMOtherm software in non-polar medium.

Calculated stable solubility of neutral and resultant IL compounds based on LLE point in non-polar model base oil (n-hexadecane), concentration by mass fraction (g/g), level of parameterization=TZVP-fine, at 2 different temperatures (25° C. and 60° C.). The LLE point in mass fraction (g/g) at 25° C. was 2 $2.3021\times10^{-14}$, while the LLE point in mass fraction (g/g) at 60° C. was $7.7597\times10^{-13}$.

Deprotonation of the acid-ester unsurprisingly drastically increased the polarity of the species (which is desired to be an effective FM) but also reduces the solubility in non-polar medium. In contrast to the results for ionic liquids comprising more than one carboxylate group, the ILN18-MECA 1 gave a hazy but stable solution in ETRO 4+(the di- and tri-carboxylate analogues were completely insoluble).

Tribology Evaluation

High Frequency Reciprocating Rig (HFRR): tribology test rubbing of ball to disc metal specimens, under pure sliding contact (boundary lubrication regime), load at 400 g, frequency at 20 Hz, temperature at 120° C. for 60 mins. Reported values were the average of minimum 2 replicate runs.

Results for 1 wt % ILN18-MECA-1 in Non-Polar Group III+ Base Oil, PETRONAS ETRO 4+

Figure 7:
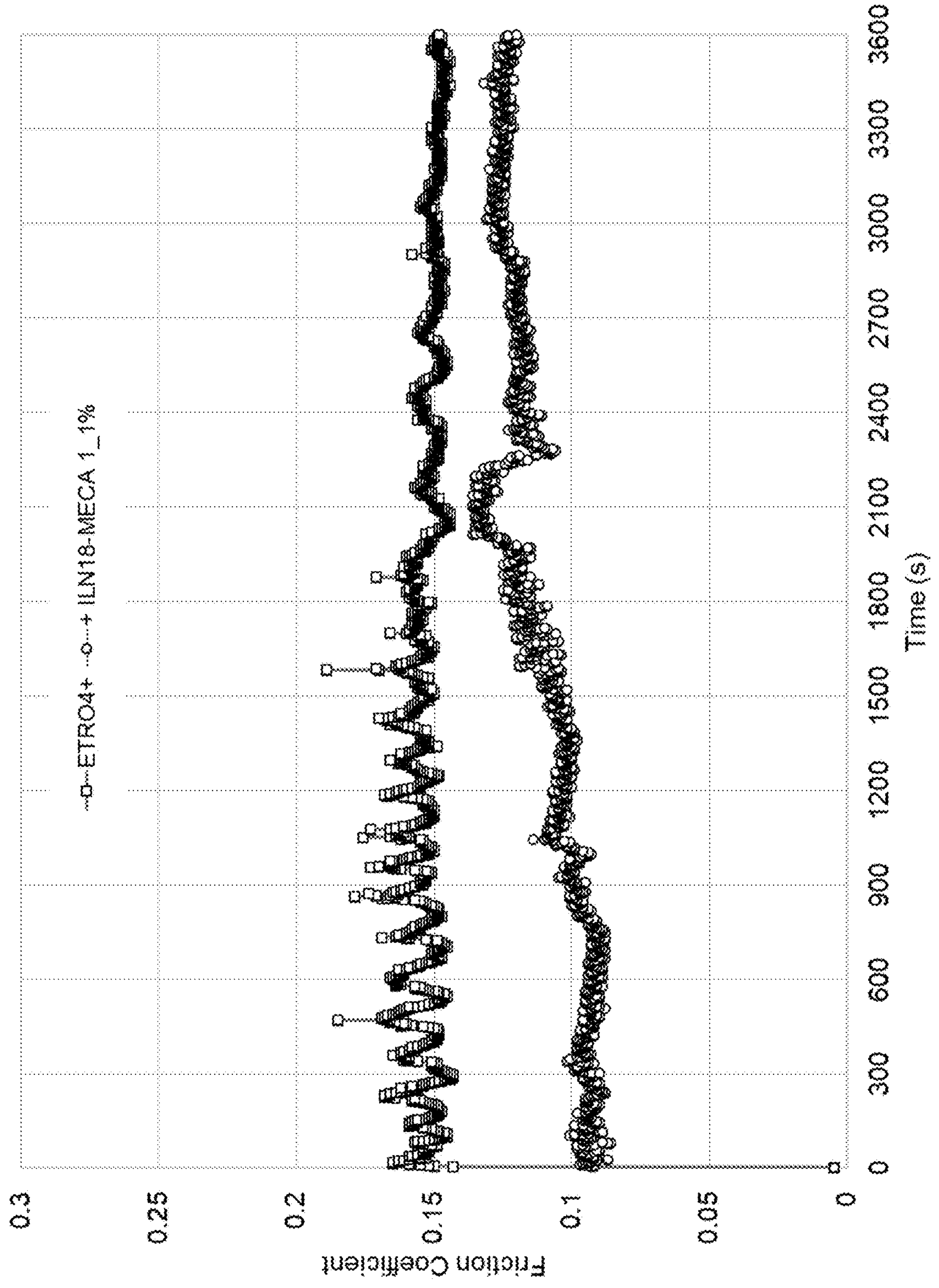
FIG. 7 shows friction coefficient behaviour for an ionic liquid according to the invention (ILN18-MECA 1) in a non-polar Group III+ base oil (ETRO 4+).

As shown in FIG. 7, ILN18-MECA 1 provided a moderate friction reducing effect in non-polar Group III+ base oil (ETRO 4+).

Figure 8:
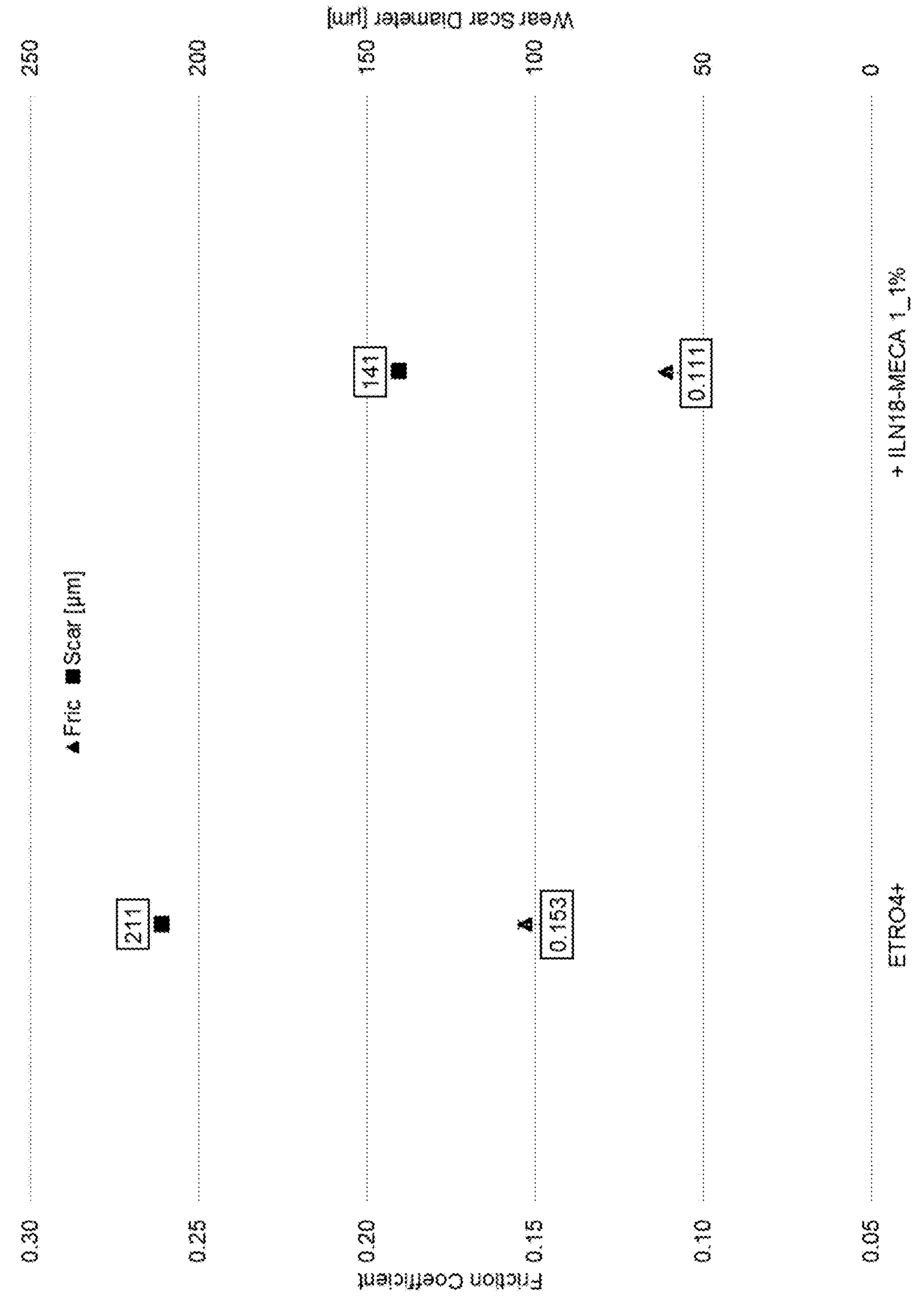
FIG. 8 shows friction coefficient average and measured scar wear diameter average for an ionic liquid according to the invention (ILN18-MECA 1) in a non-polar Group III+ base oil (ETRO 4+).

As shown in FIG. 8, ILN18-MECA 1 provided a 26% friction reduction and 18.5% wear scar reduction effect compared to the baseline fluid.

Results for 1 wt % ILN18-MECA-1 in PETRONAS LB25 Polyol Ester

Figure 9:
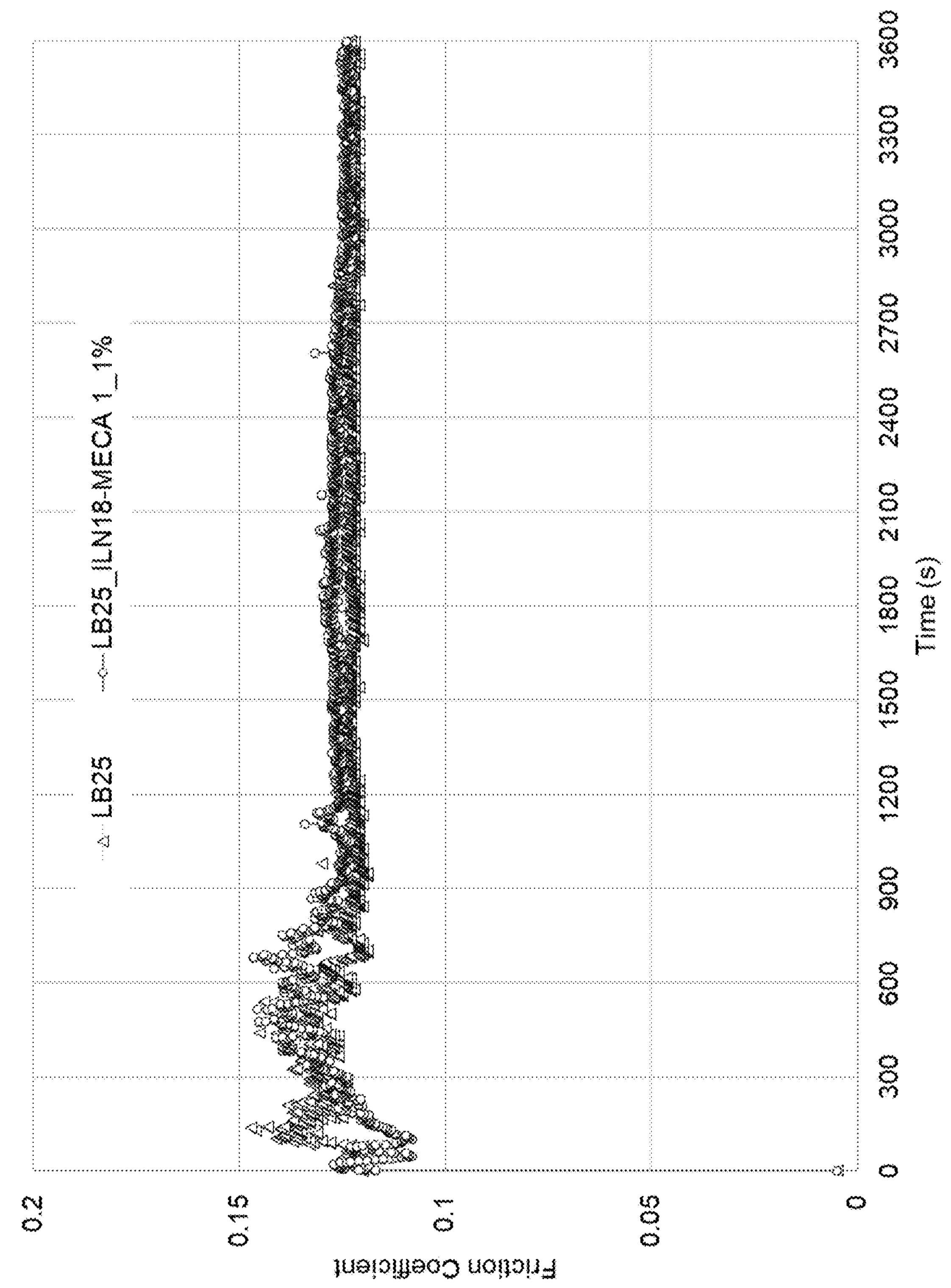
FIG. 9 shows friction coefficient behaviour for an ionic liquid according to the invention (ILN18-MECA 1) in a polar polyol ester base oil (Petronas LB25).

No friction reducing effect was observed in a polar polyol ester base oil, PETRONAS LB25 (FIG. 9).

Figure 10:
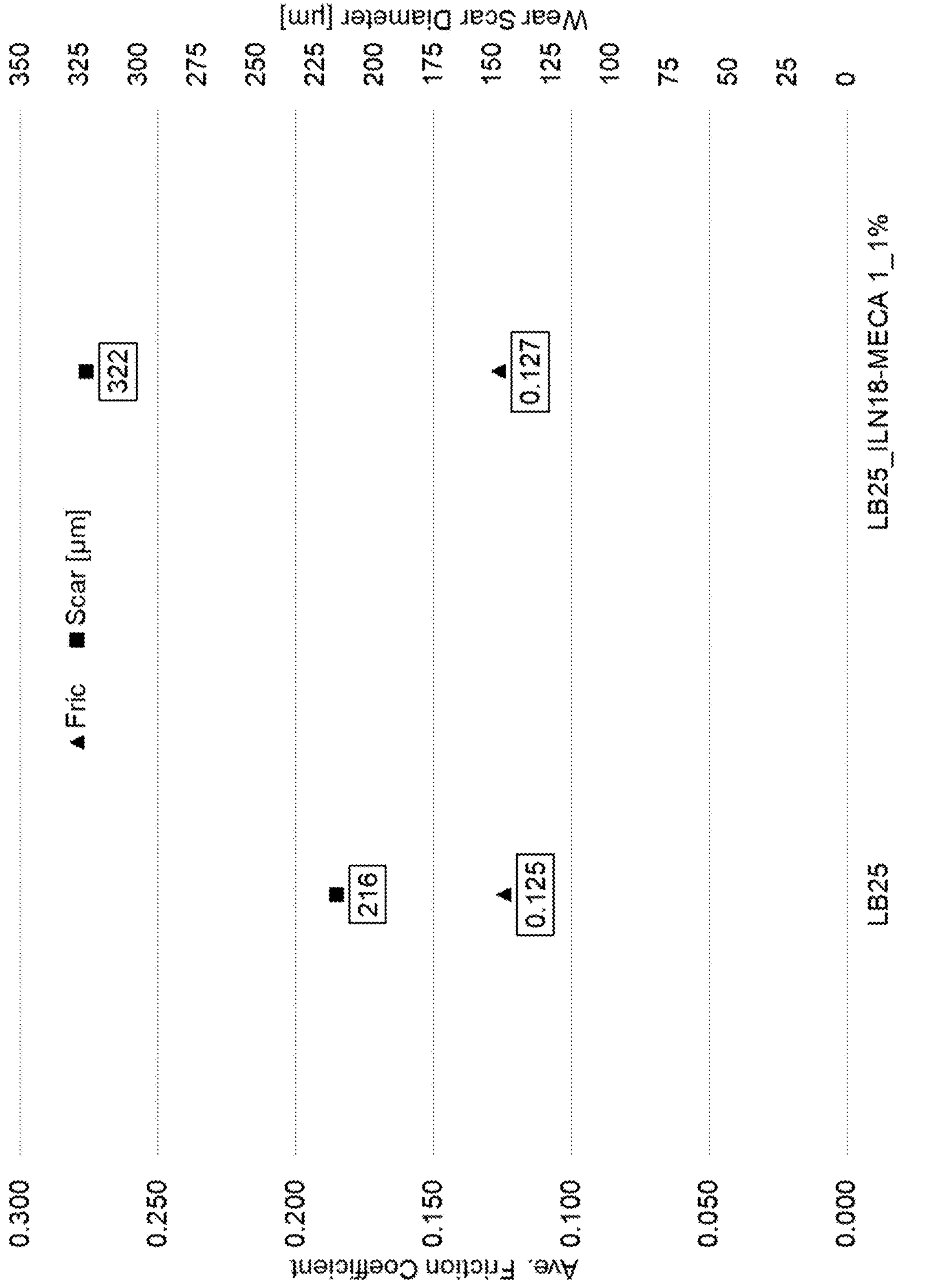
FIG. 10 shows friction coefficient average and measured scar wear diameter average for an ionic liquid according to the invention (ILN18-MECA 1) in a polar polyol ester base oil (Petronas LB25).

As shown in FIG. 10, a 1.6% increase in friction and 33% increase in wear scar diameter was observed in polar polyol ester base oil LB 25. The results suggest an antagonistic effect between the two components and demonstrate the importance of tuning the ionic liquid to the base fluid in question.

Example 10: Tunability of Ionic Liquids and Calculated Properties

Two methods were used to determine calculated values, which were used to demonstrate the tuneable polarity level of ester-acid precursors and the solubility of resultant ILs.

1. Ester Acid Precursors
   - Partition Coefficient (Log P): is the ratio of the concentration of a substance in one medium or phase ($C_1$, typically organic solvent e.g. octanol) to the concentration in a second phase ($C_2$, typically water) when the two concentrations are at equilibrium; that is, partition coefficient=$(C_1/C_2)_{equil}$
   - Predicted values were obtained from quick Log P calculation using Log P feature available in ACD/Labs software
   - Higher values indicating lower polarity (higher solubility in octanol than water) and vice versa.
   - Mostly applicable for neutral-charged compounds only
2. Ester-Carboxylate Ionic Liquids
   - Liquid-liquid equilibrium (LLE) point: composition of 2 different pure liquids which are partially miscible and placed in contact with one another and allowed to come to thermal, mechanical and transfer equilibrium in mole/mass fractions.
   - Calculation by COSMOtherm software—which has the feature that allows LLE point calculation specifically for ionic liquids/salts in a solvent.
   - Calculation parameters:
     - Parameterization level (Quantum chemical level): TZVPD-FINE
     - Temperature: 25° C./298.15 K and 60° C./333.15 K (Isothermal)—simulating standard room temperature and blending temperature
     - Model non-polar base oil/solvent to demonstrate solubility: n-hexadecane
     - LLE point: concentration by mass fraction (g of IL per g of solvent)

Results and Discussion

Polarity and Solubility of Ester Acids (IL Precursors)

Log P is one of the properties that describes the polarity of molecules. This property is one of the properties available in Safety Data Sheets (SDS), widely applied in pharmaceutical industries to understand chemical solubility in fat tissues i.e., distribution of drugs within the body. It is also applied in predicting toxicology/bioaccumulation of chemicals in either hydrophobic or hydrophilic phases. In actual experiment, known amount of the compounds in a solution were mixed and separated (typically octanol and water), and let to settle separate prior to determining their concentrations in respective phases.

ACD/Labs has the feature to quickly calculate the log P values of the compounds by including and combining algorithms (classic, GALAS and consensus model) best suited to the structure, which are the data being presented in this document. Prior to applying this, validation from multiple known compounds of calculated values versus experimental values (from SDS) have been performed to determine accuracy, and it was found that it the calculation is 99% accurate compared to experimental values.

Starting with the acids, Table 1 shows calculated Log P values of some dicarboxylic acids and mono-acids. Converting the acids into esters expands the tunability of these starting materials in terms of polarity—both addressing solubility and IL reactivity characteristics. As shown in Table 1, the clog Ps of the short chain acids and alcohols are very low, indicating their solubility in water. For longer acids and alcohols such as oleic acids and stearoyl alcohol, the hydrophobicity is higher. Combining the right type and ratios of acids and alcohols will result in a broader range of ester-carboxylate esters/anions, categorised herein as follows:

1. Mono(ester-carboxylate) anion: MECA
2. Di(ester-carboxylate) anion: DECA
3. Tri(ester-carboxylate) anion: TECA
4. Quarter(ester-carboxylate) anion: QECA

TABLE 1

Calculated Log P of certain acid and alcohol precursors

| Designation | Chemical structure | cLog P |
|---|---|---|
| Succinic acid | 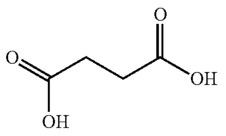 | 0.59 ± 0.23 |
| Adipic acid | 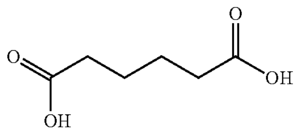 | 0.08 ± 0.21 |
| Azelaic acid | 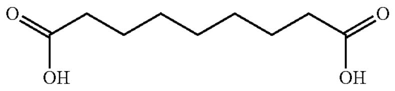 [SMILES: O=C(O)CCCCCCCC(=O)O] | 1.33 ± 0.20 |
| Sebacic acid | 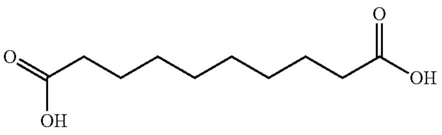 [SMILES: O=C(O)CCCCCCCCC(=O)O] | 1.86 ± 0.20 |

TABLE 1-continued

| Calculated Log P of certain acid and alcohol precursors | | |
|---|---|---|
| Designation | Chemical structure | cLog P |
| Dodecanedioic acid | 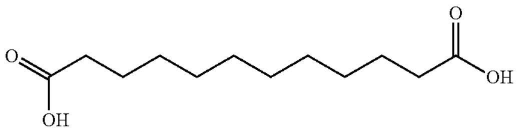 [SMILES: O=C(O)CCCCCCCCCCC(=O)O] | 2.92 ± 0.20 |
| Decanoic acid | 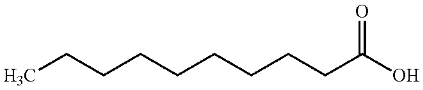 | 3.97 ± 0.18 |
| Oleic acid | 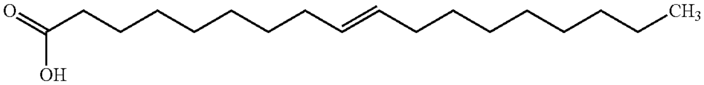 [SMILES: CCCCCCCC/C=C/CCCCCCCC(=O)O] | 7.70 ± 0.20 |
| Stearic acid | 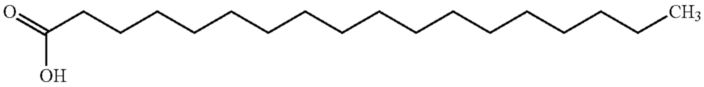 [SMILES: CCCCCCCCCCCCCCCCCC(=O)O] | 8.22 ± 0.19 |
| 1-decanol | 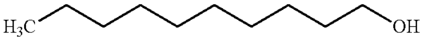 | 4.06 ± 0.18 |
| 1-stearoyl | 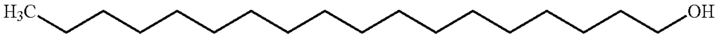 [SMILES: CCCCCCCCCCCCCCCCCCO] | 8.31 ± 0.18 |
| 1,5 pentanediol | 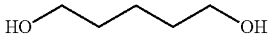 | −0.60 ± 0.19 |
| Neopentyl glycol | 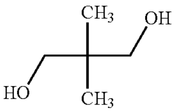 | −0.34 ± 0.47 |
| Trimethylolpropane | 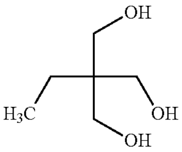 | −0.85 ± 0.65 |
| Pentaerythritol | 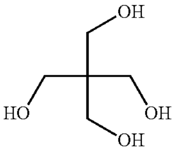 | −2.36 ± 0.85 |

Starting with MECA ester acids, examples in Table 2 below shows the higher log P in general, due to relatively lower overall polarity contributed by the single ester and single dicarboxylic group. The hydrophobicity of MECA can be further increased by choosing longer acids/alcohols. By way of example, the clog P value of n-hexadecane is 9.26, therefore in theory, MECA is more soluble in non-polar fluids such as mineral-based lubricant base oil with higher amounts of alkanes.

TABLE 2

| Calculated Log P of some examples of MECA ester acids | | |
|---|---|---|
| Designation | Chemical structure | cLog P |
| MECA-1 (decanoyl mono azelate) | 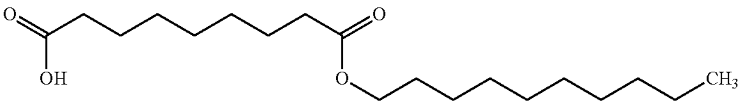 [SMILES: CCCCCCCCCCOC(=O)CCCCCCCC(=O)O] | 6.58 ± 0.22 |

TABLE 2-continued

| Calculated Log P of some examples of MECA ester acids | | |
|---|---|---|
| Designation | Chemical structure | cLog P |
| MECA-2 (stearoyl mono azelate) | 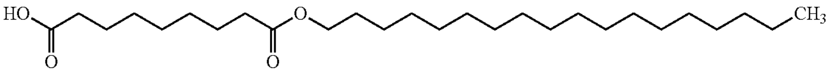 [SMILES: CCCCCCCCCCCCCCCCCCOC(=O)CCCCCCCC(=O)O] | 10.83 ± 0.22 |
| MECA-4 (12 nonanoate hydroxy stearic) | 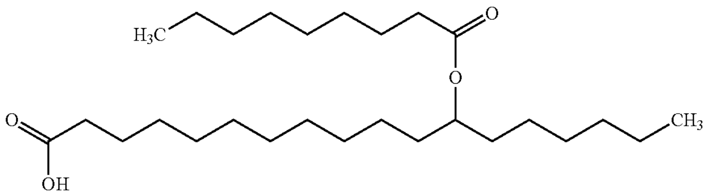 [SMILES: CCCCCCCCC(=O)OC(CCCCCC)CCCCCCCCCCC(=O)O] | 10.64 ± 0.22 |
| MECA-5 (Oleyl mono azelate) | 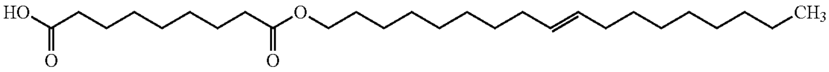 [SMILES: CCCCCCCC/C=C/CCCCCCCCOC(=O)CCCCCCCC(=O)O] | 10.31 ± 0.22 |

Table 3 below shows clog P values of DECA esters, which require the use of at least diols to form 2 carboxylate and 2 ester groups. As expected, the c Log P values are lower than MECA due to the increase in overall polarity. Therefore, it is expected that the solubility of these esters decreases in non-polar base oils as the delta clog P compared to e.g., n-hexadecane, increases. These types of esters could be more suitable to be used in more polar fluids such as diesters and polyol esters, or applications which requires higher reactivity/tribo-action. Within DECA, the hydrophobicity can be adjusted slightly by changing the central diol linearity or by increasing the carbon chain length of the dicarboxylic acids.

TABLE 3

| Calculated Log P of some examples of DECA ester acids | | |
|---|---|---|
| Designation | Chemical structure | cLog P |
| 5B-DC4 (neopentyl glycol disuccinate) | 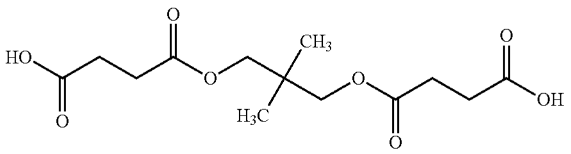 [SMILES: CC(C)(COC(=O)CCC(=O)O)COC(=O)CCC(=O)O] | 0.29 ± 0.54 |
| 5B-DC10 (neopentyl glycol disebacate) | 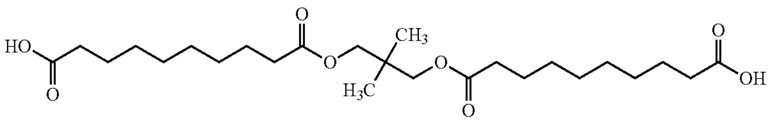 [SMILES: CC(C)(COC(=O)CCCCCCCCC(=O)O)COC(=O)CCCCCCCCC(=O)O] | 5.35 ± 0.26 |
| 5L-DC10 (1,5-pentanediol disebacate) | 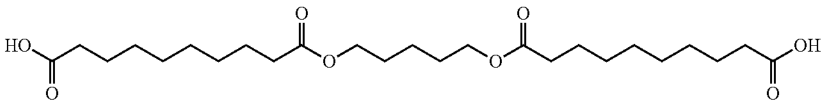 [SMILES: O=C(O)CCCCCCCCC(=O)OCCCCCOC(=O)CCCCCCCCC(=O)O] | 5.49 ± 0.24 |
| 5B-DC12 (neopentyl glycol didodecanedioate) | 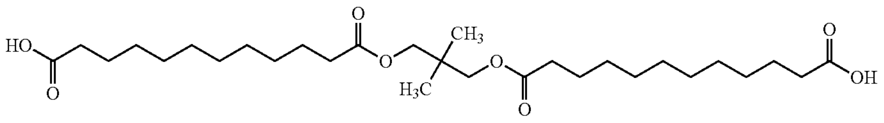 [SMILES: CC(C)(COC(=O)CCCCCCCCCCC(=O)O)COC(=O)CCCCCCCCCCC(=O)O] | 7.48 ± 0.26 |

For TECA, 2 examples are as shown below. Although relatively high clog Ps, the overall polarity is still considered high with respect to the molecular weight of the ester acids, each molecule of which includes three dicarboxylic acids. Similar results arise for QECA (Table 5).

TABLE 4

Calculated Log P of some examples of TECA ester acids

| Designation | Chemical structure | cLog P |
|---|---|---|
| 6BT-DC10 (trimethylolpropane trisebacate | 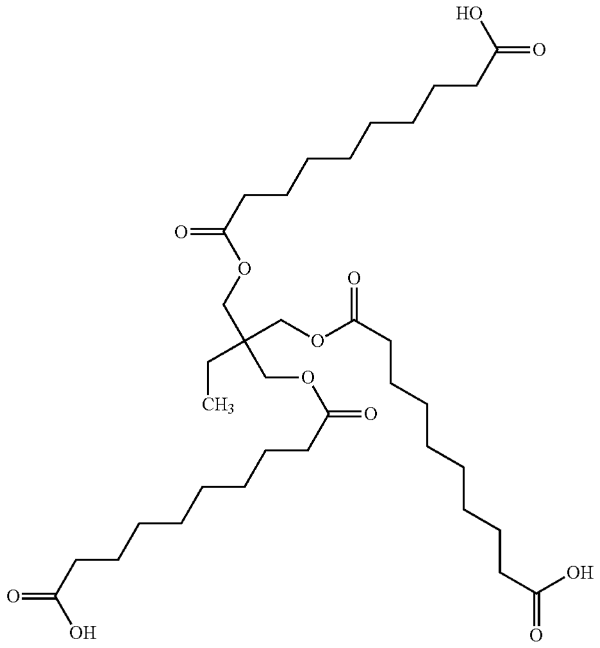 [SMILES: CCC(COC(=O)CCCCCCCCC(=O)O)(COC(=O)CCCCCCCCC(=O)O)COC(=O)CCCCCCCCC(=O)O] | 7.39 ± 0.28 |
| 3G-DC10 (glycerol trisebacate) | 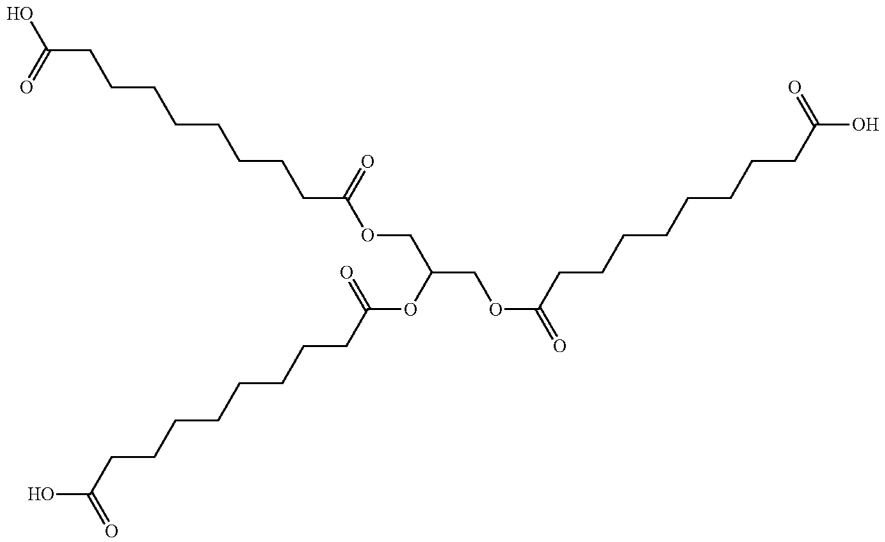 [SMILES: O=C(O)CCCCCCCCC(=O)OCC(COC(=O)CCCCCCCCC(=O)O)OC(=O)CCCCCCCCC(=O)O] | 6.20 ± 0.28 |

TABLE 5

| Calculated Log P of an example of QECA ester acids | | |
|---|---|---|
| Designation | Chemical structure | cLog P |
| 4PE-DC10 (pentaerythritol pentasebacate) | 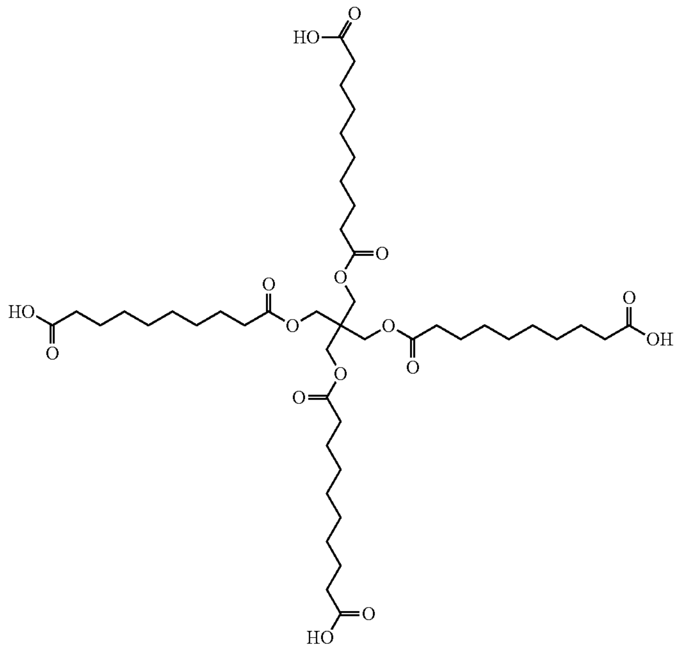 [SMILES: O=C(O)CCCCCCCCC(=O)OCC(COC(=O)CCCCCCCCC(=O)O)(COC(=O)CCCCCCCCC(=O)O)COC(=O)CCCCCCCCC(=O)O] | 8.59 ± 0.37 |

Prediction of Ionic Compounds Using c Log P

For all the compounds earlier described, the values obtained were for neutral compounds, and not the charged species that exist in aqueous solutions/in ionic liquids. However, the software used was not able to provide calculated Log P values for the ionic species that were technically sensible (no change to polarity of carboxylate esters was predicted by the software).

One exception to this was observed for ionic amino species. Thus, a change in polarity was predicted for trioctyl amine vs. the quaternary trioctylmethyl ammonium cation. This cationic species is denoted as ILN18 herein.

The c Log P for trioctylamine was 11.22±0.22, while the c Log P for quaternary trioctylmethyl ammonium was 2.63±0.23. It can be seen here that the polarity drastically changes once the compound is in cationic form, by more than 75%. Therefore, the hypothesis was this should be reflective also with the anionic analogues of the ester acids.

The presented c Log P values demonstrate that the polarity of ester acids can be customised by choosing the right compounds and their ratios, according to final target application/environment. Most importantly, these values will feed into the design of resultant ILs.

A more accurate way to predict solubility of ILs derived from these esters is by determining the liquid-liquid equilibrium (LLE) points of mixtures with desired solvent, especially for IL compounds. Therefore, predictions were calculated using COSMOtherm software that has such available feature.

Polarity and Solubility of Ester-ILs

The solubility of ester-ILs were predicted based on LLE point, with 2 fixed cations respectively (trioctylmethyl ammonium, designated as ILN18 and trioctylmethyl phosphonium, designated as ILP18) in non-polar model base oil (n-hexadecane). LLE point values were described as concentration by mass fraction (g/g in solvent). Both are calculated at room temperature as well as blending temperature of 60° C. All LLE of the ILs were calculated based on equimolar ratio between the cation and the anions e.g., 1 mole of ILN18 to a mole of MECA esters and 2 moles of ILN18 to a mole of DECA ester/dicarboxylic acids. As shown in Table 6, Table 7 and Table 8, the first 2 compounds are reference ILs for DECA and MECA esters, without the presence of ester groups.

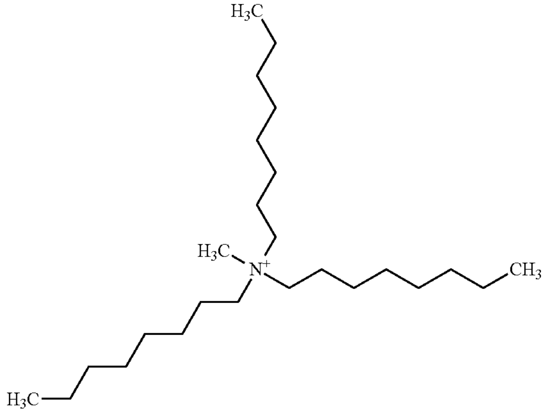

Trioctylmethyl ammonium

-continued

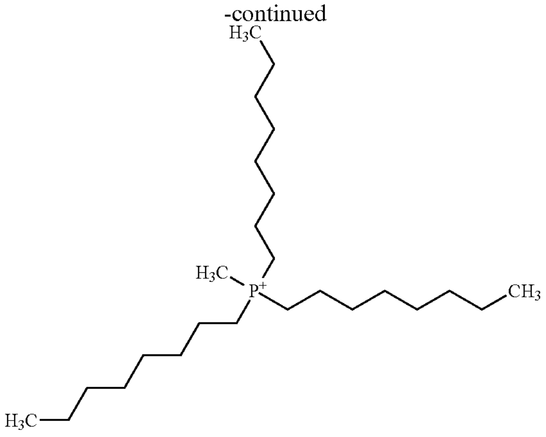

Trioctylmethyl phosphonium

The overall predicted equilibrium points of all ILs calculated were very low, therefore the polarity and solubility are relatively compared against 1) the model base oil (n-hexadecane), 2) ILs of corresponding mono/dicarboxylate anions) and 3) between MECA-IL and DECA-IL compounds. LLE point of TECA (and above) somehow cannot be determined (unable to convert into compatible input file) using the same method hence is not discussed.

TABLE 6

Calculated LLE points by mass fraction of some dicarboxylate and DECA-based ILs (in combination with trioctylmethyl ammonium cation, ILN18) with respect to n-hexadecane as non-polar solvent

| Compound | Solubility in n-hexadecane (25° C.) | Solubility in n-hexadecane (60° C.) | Remark |
|---|---|---|---|
| ILN18-DC10 | $3.9906 \times 10^{-21}$ | $7.404 \times 10^{-19}$ | Disebacate anion IL<br>No ester group<br>Deprotonated compound<br>Limited/fixed polarity |
| ILN18-DC12 | $2.5257 \times 10^{-20}$ | $3.8709 \times 10^{-18}$ | Didodecanedioate anion IL<br>No ester group<br>Deprotonated compound<br>Limited/fixed polarity |
| ILN18-5B-DC10 | $2.1746 \times 10^{-19}$ | $2.7671 \times 10^{-17}$ | Higher solubility in n-hexadecane increased by 2 decimal points |
| ILN18-5L-DC10 | $2.9116 \times 10^{-19}$ | $3.5879 \times 10^{-17}$ | Lower polarity than ILN18- DC12<br>Linear central alcohol gives higher solubility |
| ILN18-5B-DC12 | $2.5107 \times 10^{-19}$ | $3.157 \times 10^{-17}$ | Increasing dicarboxylic chain length has minimal impact on solubility in base oil compared to changing central alcohol from branched to linear |

TABLE 7

Calculated LLE points by mass fraction of some mono, di and MECA-based ILs (in combination with trioctylmethyl ammonium cation, ILN18) with respect to n-hexadecane as non-polar solvent

| Compound | Solubility in n-hexadecane (25° C.) | Solubility in n-hexadecane (60° C.) | Remark |
|---|---|---|---|
| ILN18-MC9 | $2.176 \times 10^{-14}$ | $7.1978 \times 10^{-13}$ | Comparative monocarboxylate (nonanoate) IL to MECA-1 |
| ILN18-MC10 | $2.4817 \times 10^{-14}$ | $8.1015 \times 10^{-13}$ | Comparative monocarboxylate (decanoate) IL to MECA-1 |
| ILN18-MC18 | $3.5043 \times 10^{-14}$ | $1.1005\ 10^{-12}$ | Comparative monocarboxylate (stearate) IL to MECA-1 |

TABLE 7-continued

Calculated LLE points by mass fraction of some mono, di and MECA-based ILs (in combination with trioctylmethyl ammonium cation, ILN18) with respect to n-hexadecane as non-polar solvent

| Compound | Solubility in n-hexadecane (25° C.) | Solubility in n-hexadecane (60° C.) | Remark |
|---|---|---|---|
| ILN18-MC19 | $3.7733 \times 10^{-14}$ | $1.1813 \times 10^{-12}$ | Comparative monocarboxylate (nonadecanoic) IL to MECA-1 |
| ILN18-DC9 | $4.066 \times 10^{-21}$ | $7.517 \times 10^{-19}$ | Comparative dicarboxylate (azelate) IL to MECA-1 |
| ILN18-MECA-1 | $2.3021 \times 10^{-14}$ | $7.7597 \times 10^{-13}$ | Significant improvement in IL solubility in model base oil due to reduced overall polarity |
| ILN18-MECA-2 | $2.3524 \times 10^{-14}$ | $7.7991 \times 10^{-13}$ | Slight increase in solubility with longer alcohol chain |
| ILN18-MECA-4 | $3.249 \times 10^{-14}$ | $1.0544 \times 10^{-12}$ | “branched”/protected location of ester group possibly helped with solubility |

When comparing ILN18-DC10 and ILN18-5B-DC10, the addition of 2 moles of ester compounds which bridges the 2 terminal carboxylate groups increases the solubility of the ester ILs by 2 decimal points. For the same alcohol carbon number, by simply changing the central alcohol from branched to linear (ILN18-5B-DC10 to ILN18-5L-DC10), slight increase of solubility in n-hexadecane can be seen and is slightly higher solubility than adding 2 extra carbon atoms respectively in the dicarboxylate moiety (ILN-5B-DC12). This indicates the impact of asymmetricity of the central anions played more part in reducing overall polarity of the anions than symmetric configuration despite being bulkier. Therefore, combining ester and alcohols provide more flexibility to customise the IL polarity, especially towards lower polarity, which cannot be achieved significantly simply by extending the carbon number of the acids. This is the key advantage of the overall concept.

Further reduction of anion polarity through MECA compounds resulted in drastic rise in solubility in n-hexadecane. ILN18-MECA-1 for example, has solubility by 7 decimal points higher when compared to ILN18-DC10 and at least by 5 decimal points higher to ILN18-5B-DC10/ILN18-5L-DC10. Comparing further against IL with mono-carboxylate IL of the same carbon chain length (nonanoate, ILN18-MC9) and one carbon atom higher (decanoate, ILN18-MC10), ILN18-MECA-1 has intermediate solubility between the 2 ILs, creating new polarity/solubility window within carboxylate-based ILs analogues.

When comparing between MECA-ILs, extending the carbon chain of the alcohol even by 8 carbon number (ILN18-MECA-2 against ILN18-MECA-1) does not significantly increase to the overall solubility of the IL in n-hexadecane. Interestingly, for the same anion carbon number, the position of the C—O bond from the ester linkage, attached to the tertiary carbon position of the acid has shown to affect the solubility more significantly than adding more carbons to the alcohol.

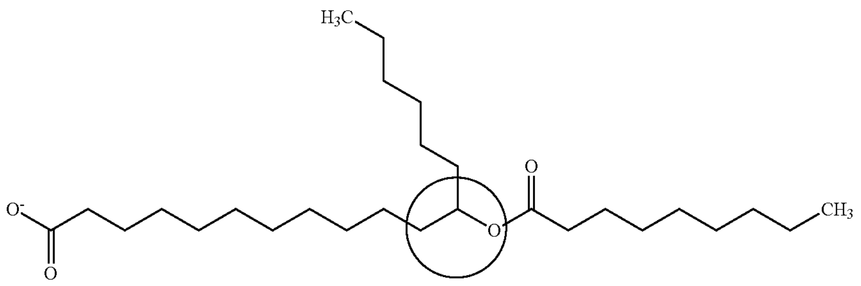 [SMILES: CCCCCCCCC(=O)OC(CCCCCC)CCCCCCCCCCC(=O)[O-]]

Position of C—O linkage of the ester group in IL with MECA-4 anion resulted in slightly higher solubility in nonpolar model oil.

Simply to validate the solubility values usually observed for equivalent phosphonium ILs, trioctylmethyl phosphonium cation (ILP-18) combined with as few ester anions chosen from Table 6 were calculated, as shown in Table 8. As predicted, having phosphonium as the centre atom of the cation slightly increase the solubility of the ILs in hexadecane usually associated to the lower charge density of phosphonium cations as compared to ILN18 analogues.

TABLE 8

| Calculated LLE points by mass fraction of some ester-based ILs (in combination with trioctylmethyl phosphonium cation, ILP18) with respect to n-hexadecane as non-polar solvent | | | |
|---|---|---|---|
| Compound | Solubility in n-hexadecane (25° C.) | Solubility in n-hexadecane (60° C.) | Remark |
| ILP18-DC10 | 5.9339 × 10–21 | 1.0384 × 10–18 | Base polarity |
| ILP18-DC12 | 3.7647 × 10–20 | 5.4372 × 10–18 | Base polarity |
| ILP18-5B-DC10 | 3.3764 × 10–19 | 4.0327 × 10–17 | Phosphonium cations |
| ILP18-5L-DC10 | 4.5279 × 10–19 | 5.2366 × 10–17 | have higher solubility than |
| ILP18-5B-DC12 | 3.9162 × 10–19 | 4.6196 × 10–17 | ammonium of the same |
| ILP18-MECA-1 | 3.407 × 10–14 | 1.0856 × 10–12 | alkyl groups and anions |

Example 11: Miscibility of Ionic Liquids

Synthesised ionic liquids (1 wt. %) were mixed with ETRO 4+ solution at 60° C. for 1 h, and left to sit for 24 h before observation.

TABLE 9

| Results of miscibility studies | |
|---|---|
| Ionic liquid | Appearance |
| ILN18-DC12 | Insoluble (2 separate phases) |
| ILN18-5B-DC10 | Insoluble (2 separate phases) |
| ILP18-5B-DC10 | Insoluble (crashed out droplets on glass walls) |
| ILN18-MECA-1 | Hazy solution but stable (no sedimentation) |
| ILN18-MECA-2 | Hazy solution but stable (no sedimentation) |
| ILN18-MECA-4 | Clear solution |

As shown in Table 9, ILs from different IL groups were tested for their solubility at 1 wt % in ETRO 4+. The visual appearances show the same trend as the c Log P based predicted solubility.

The results demonstrate the efficacy of ionic liquids disclosed here in the reduction of friction in base fluids.

The results also demonstrate the tuneable polarity of ester-carboxylate ILs based on the number of ester and carboxylate groups. A range of ester-carboxylate ionic liquids, denoted herein as MECA, DECA, TECA and QECA have been evaluated by clog P and LLE points calculation both as neutral ester-acid compounds and their resultant ILs (MECA and DECA), respectively. It has been proven that by selecting the right precursors, certain window of IL polarity can be achieved, to suit intended final solubility that cannot be achieved from the carboxylic acids alone.

The invention claimed is:

1. An ionic liquid comprising:

an anionic portion that is selected from one or more of formula Ia or formula Ic:

Ia

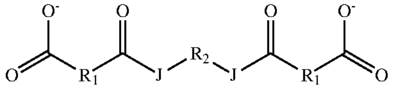

Ic

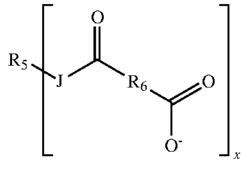

wherein:

x is an integer of 3;

each $R_1$ is independently selected from a linear, branched or cyclic $C_1$-$C_{20}$ aliphatic hydrocarbyl group that is saturated or unsaturated, a $C_6$-$C_{10}$ aryl group, and a 5-10 membered heteroaromatic ring system;

$R_2$ is selected from the group consisting of a linear, branched or cyclic $C_1$-$C_{40}$ aliphatic hydrocarbyl group that is saturated or unsaturated, a linear or branched $C_2$-$C_{40}$ polyalkyleneglycol group, a $C_6$-$C_{22}$ aryl group, a moiety formed by removing two hydroxyl groups from a sugar alcohol, and a moiety formed by removing two hydroxyl groups from a dehydrated sugar alcohol or isosorbide;

$R_5$ is selected from the group consisting of a linear, branched or cyclic $C_1$-$C_{20}$ aliphatic hydrocarbyl group that is saturated or unsaturated, a linear or branched $C_2$-$C_{20}$ polyalkyleneglycol group, a $C_6$-$C_{22}$ aryl group, a moiety formed by removing x hydroxyl groups from a sugar alcohol, and a moiety formed by removing x hydroxyl groups from a dehydrated sugar alcohol; and each $R_6$ independently represents a linear, branched or cyclic $C_1$-$C_{20}$ aliphatic hydrocarbyl group that is saturated or unsaturated, wherein for each of $R_1$, $R_2$, $R_5$ and $R_6$:

each of the $C_1$-$C_{20}$ aliphatic hydrocarbyl group, $C_1$-$C_{40}$ aliphatic hydrocarbyl group, $C_2$-$C_{40}$ polyalkyleneglycol group, and $C_2$-$C_{20}$ polyalkyleneglycol group are not interrupted or are interrupted by one or more groups selected from an aromatic or non-aromatic ring system having from 5 to 14 atoms, an ester group, an amide group, and a carbamate group, and each of the $C_1$-$C_{20}$ aliphatic hydrocarbyl group, $C_1$-$C_{40}$ aliphatic hydrocarbyl group, $C_2$-$C_{40}$ polyalkyleneglycol group, $C_2$-$C_{20}$ polyalkyleneglycol group, and $C_6$-$C_{22}$ aryl group are unsubstituted or substituted by one or more groups selected from the group consisting of hydroxyl, primary amino, secondary amino and tertiary amino, where the secondary and tertiary amino groups are substituted by one or two $C_{1-10}$ hydrocarbyl groups, respectively; and each J independently represents O or NRN, where RN represents H or a $C_1$-$C_{18}$ alkyl or alkenyl group a cationic portion having formula A:

$$(X)_n^{a+},$$ A where:

X represents a cationic species; and a and n are selected to approximately balance the charge of the ionic liquid, wherein the ionic liquid is ashless.

2. The ionic liquid according to claim 1, wherein one or more of the following applies:

(a) each $R_1$ is independently selected from a phenyl group, a furan group or, more particularly, a linear or branched $C_4$-$C_{18}$ aliphatic hydrocarbyl group that is saturated or unsaturated;

(b) $R_2$ is a moiety formed by removing both hydroxyl groups from isosorbide, or more particularly, a linear or branched $C_2$-$C_{20}$ aliphatic hydrocarbyl group, or a linear or branched $C_2$-$C_{20}$ polyalkyleneglycol, where the linear or branched $C_2$-$C_{20}$ aliphatic hydrocarbyl group and the linear or branched $C_2$-$C_{20}$ polyalkyleneglycol are saturated or unsaturated, where the linear or branched $C_2$-$C_{20}$ aliphatic hydrocarbyl group and the linear or branched $C_2$-$C_{20}$ polyalkyleneglycol are not interrupted or is interrupted by one or more groups selected from an aromatic or non-aromatic ring system having 5 or 6 atoms, an amide group, and a carbamate group;

(c) $R_5$ is selected from the group consisting of a linear or branched $C_3$-$C_{14}$ aliphatic hydrocarbyl group that is saturated or unsaturated, a $C_6$-$C_{10}$ aryl group, a moiety formed by removing x hydroxyl groups from a sugar alcohol, and a moiety formed by removing x hydroxyl groups from a dehydrated sugar alcohol; and (d) each $R_6$ is independently selected from a phenyl group, a furan group or, more particularly, a linear or branched $C_4$-$C_{18}$ aliphatic hydrocarbyl group that is saturated or unsaturated.

3. The ionic liquid according to claim 1, wherein one or more of the following applies:

(a) each $R_1$ independently represents a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid;

(b) each J represents O and $R_2$ is a group formed by removing two hydroxyl groups from a compound selected from the following:

neopentyl glycol, 1,5-pentanediol, 1,9-nonanediol, 1,6-hexanediol, 2-methyl-1,3-propanediol, 2,5-hexanediol, 2,7-octanediol, a saturated straight chain $C_{28}$ 1,14-diol, an unsaturated straight chain $C_{28}$ 1,14-diol,

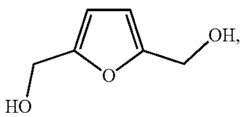

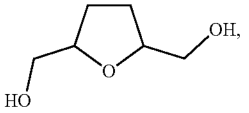

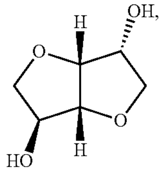

-continued

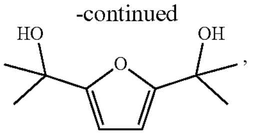

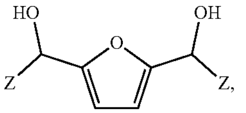

and

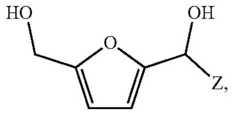

where each Z independently represents a $C_1$ to $C_{12}$ aliphatic hydrocarbyl group;

(c) one of the following applies:

$R_2$ represents a $C_{4-16}$ alkylene group and each J represents NH; or $R_2$ represents propylene, one J represents NH and the other J represents $NR_N$ where $R_N$ represents oleyl;

(d) $R_5$ is selected from the group consisting of a phenyl ring, and a branched $C_3$-$C_{10}$ aliphatic group; and (e) each $R_6$ independently represents a moiety formed by removing both carboxylic acid groups from a compound selected from the list consisting of oxalic acid, malonic acid, succinic acid, glutaric acid, adipic acid, pimelic acid, suberic acid, azelaic acid, sebacic acid, 1,12-dodecanedioic acid, 1,18-octadecanedioic acid, terephthalic acid, isophthalic acid, phthalic acid, and 2,5-furandicarboxylic acid.

4. The ionic liquid according to claim 1, wherein:

$R_5$ is a moiety formed by removing three hydroxyl groups from a compound selected from the group consisting of trimethylolpropane, glycerol, pyrogallol, hydroxyquinol, phloroglucinol, and 3-methylpentane-1,3,5-triol.

5. The ionic liquid according to claim 1, wherein $R_2$ represents a branched alkylene group

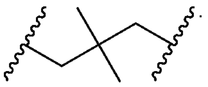 [SMILES: *CC(C)(C)C*]

6. The ionic liquid according to claim 1, wherein $R_5$ represents a branched group

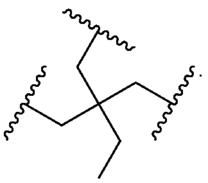 [SMILES: *CC(C*)(C*)CC]

7. The ionic liquid according to claim 1, wherein the anionic portion is of formula Ia.

8. The ionic liquid according to claim 1, wherein the anionic portion is of formula Ic and has the structure:

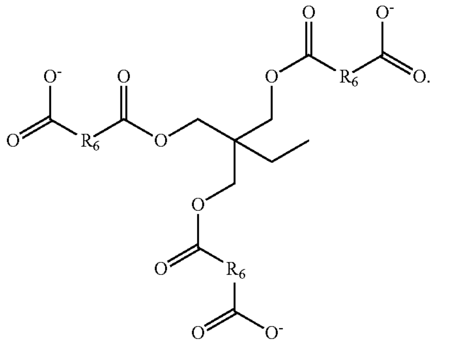

9. The ionic liquid according to claim 1, wherein the cationic portion is selected from one or more of the group consisting of a quaternary phosphonium cation, a quaternary sulphonium cation, a quaternary ammonium cation comprising at least one amide group, a quaternary ammonium cation comprising at least one ester group, a substituted quaternary imidazolium cation comprising at least one ester group, a substituted quaternary imidazolium cation comprising at least one alkyleneglycol group, a substituted quaternary imidazolium cation comprising at least one amide group, azaannulenium, azathiazolium, benzimidazolium, benzofuranium, benzothiophenium, benzotriazolium, borolium, cinnolinium, diazabicyclodecenium, diazabicyclononenium, 1,4- diazabicyclo [2.2.2]octanium, diazabicyclo-undecenium, dibenzofuranium, dibenzothiophenium, dithiazolium, dithiazolium, furanium, guanidinium, imidazolium, indazolium, indolinium, indolium, morpholinium, oxaborolium, oxaphospholium, oxazinium, oxazolium, iso-oxazolium, oxazolinium, pentazolium oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, isoquinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, combinations thereof, and cationic molecules comprising more than one of the foregoing.

10. The ionic liquid according to claim 1, wherein the cationic portion has the formula $[YX_3X_4X_5X_6]^+$, wherein:

Y represents N, P or S; and (a) each of $X_3$ to $X_6$ are independently selected from $C_1$ to $C_{30}$ straight chain or branched alkyl and alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$ to $X_6$ combine to form an alkylene chain $—(CH_2)_q—$ wherein q is from 3 to 6; wherein any one or more of said straight or branched chain alkyl and alkenyl groups, cycloalkyl groups, arylalkyl groups, alkylaryl groups; aryl groups or alkylene chains are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl; or (b) at least one of $X_3$ to $X_6$ have the formula $—X_7O(C{=}O)X_8$ or $—X_7(C{=}O)—O—X_8$, wherein $X_7$ is a $C_1$ to $C_{10}$ straight chain or branched alkyl or alkenyl group, or a $C_3$ to $C_6$ cycloalkyl or cycloalkenyl group; and $X_8$ is a $C_1$ to $C_{30}$ straight chain or branched alkyl or alkenyl group; a $C_3$ to $C_6$ cycloalkyl group; a $C_1$ to $C_{30}$ arylalkyl group; a $C_1$ to $C_{30}$ alkylaryl group; an aryl group; or any two respective $X_8$ groups combine to form an alkylene chain $—(CH_2)_q—$ wherein q is from 3 to 6; wherein $X_7$ and/or $X_8$ are optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl;

and wherein the other of $X_3$ to $X_6$ that are not as defined above are independently selected from $C_1$ to $C_{30}$ straight chain or branched alkyl and alkenyl groups such as $C_1$ to $C_{10}$ alkyl or alkenyl groups; $C_3$ to $C_6$ cycloalkyl groups; $C_1$ to $C_{30}$ arylalkyl groups; $C_1$ to $C_{30}$ alkylaryl groups; aryl groups; or any two of $X_3$, $X_4$, $X_5$ and $X_6$ combine to form an alkylene chain $—(CH_2)_q—$ wherein q is from 3 to 6; wherein any one or more of said straight or branched chain alkyl and alkenyl groups, cycloalkyl groups, arylalkyl groups, alkylaryl groups; aryl groups or alkylene chains is optionally substituted by one to three groups selected from: $C_1$ to $C_4$ alkoxy, $C_2$ to $C_8$ alkoxyalkoxy, $C_3$ to $C_6$ cycloalkyl, —OH, $—NH_2$, —SH, $—CO_2(C_1$ to $C_6)$alkyl, and $—OC(O)(C_1$ to $C_6)$alkyl.

11. The ionic liquid according to claim 10, wherein option (a) applies.

12. A composition comprising:

a base fluid, and an liquid as defined in claim 1.

13. A method of reducing the friction of a base fluid or of a polyol ester, said method comprising the steps:

(i) providing a base oil or a polyol ester;

(ii) mixing the base oil or polyol ester with an amount of an ionic liquid as defined in claim 1.

14. A method of preparing an ionic liquid as defined in any one of claim 1, said method comprising the steps:

(i) providing an intermediate product comprising:

an ester group or an amide group; and a carboxylic acid group (ii) converting the intermediate product to an ionic liquid by either:

(a) directly reacting the intermediate product with a cationic base;

(b) deprotonating the intermediate esters with a base to form an ester alkaline/metal salts, subsequently conducting a metathesis reaction between the ester salt with a salt compound that comprises a cationic portion having formula A; or (c) reacting the intermediate product with an alkylamine or arylamine.

15. A salt comprising:

an anionic portion as defined in claim 1, and a cationic portion comprising one or more alkali metal cations.

16. A method of preparing a salt as defined in claim 15, said method comprising the steps:

(i) reacting an alcohol with a dicarboxylic acid to produce an intermediate product comprising an ester group and a carboxylic acid group;

ii) reacting the intermediate product with a basic salt of an alkali metal to form a salt as defined in claim 15.

* * * * *